US012616435B2

(12) United States Patent
Boufahja et al.

(10) Patent No.: US 12,616,435 B2
(45) Date of Patent: May 5, 2026

(54) SYSTEMS AND METHODS FOR MEDICAL DATA TRANSMISSION USING AN AGNOSTIC APPLICATION PROGRAMMING INTERFACE

(71) Applicant: GE Precision Healthcare LLC, Wauwatosa, WI (US)

(72) Inventors: Abderrazek Boufahja, Illkirch-Graffenstaden (FR); Bouchra Youss, Strasbourg (FR); Tristan Guillevin, Rotterdam (NL)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 613 days.

(21) Appl. No.: 18/049,910

(22) Filed: Oct. 26, 2022

(65) Prior Publication Data
US 2024/0138796 A1 May 2, 2024

(51) Int. Cl.
*A61B 6/00* (2024.01)
*G16H 30/40* (2018.01)

(52) U.S. Cl.
CPC .......... *A61B 6/5217* (2013.01); *A61B 6/5294* (2013.01); *G16H 30/40* (2018.01)

(58) Field of Classification Search
CPC ..... A61B 6/5217; A61B 6/5294; G16H 30/40
See application file for complete search history.

(56) References Cited

U.S. PATENT DOCUMENTS

| | | | |
|---|---|---|---|
| 8,538,776 B2 | 9/2013 | Reiner | |
| 9,129,044 B2 | 9/2015 | Shih | |
| 9,480,448 B2 * | 11/2016 | Guntzer | A61B 6/022 |
| 10,350,438 B2 * | 7/2019 | Brooks | G06N 20/00 |
| 2010/0049549 A1 | 2/2010 | Nelms | |
| 2015/0356258 A1 | 12/2015 | Moore | |
| 2016/0110325 A1 | 4/2016 | Parikh | |
| 2018/0181716 A1 * | 6/2018 | Mander | G16H 50/20 |

(Continued)

FOREIGN PATENT DOCUMENTS

| | | | |
|---|---|---|---|
| CN | 110008173 A | 7/2019 | |
| EP | 2559382 A2 * | 2/2013 | A61B 6/4494 |

(Continued)

OTHER PUBLICATIONS

"Tableau Server Components," IntelliPaat Website, Available Online at https://intellipaat.com/blog/tutorial/tableau-tutorial/tableau-server-components/, Available as Early as Dec. 17, 2021, 4 pages.

(Continued)

*Primary Examiner* — Oneal R Mistry
*Assistant Examiner* — Rachel L Roberts
(74) *Attorney, Agent, or Firm* — McCoy Russell LLP

(57) ABSTRACT

Various methods and systems are provided for agnostic transmission of radiation information data from a database to an analytics/business-intelligence tool. A system may include memory storing instructions executable by a processor to retrieve radiation dose data in a first format from a radiation dose database via an interoperability system operably coupled to the radiation dose database, convert the radiation dose data to a second format usable by a radiation dose consumer, and generate visualizations of the radiation dose data for display on a display device.

20 Claims, 13 Drawing Sheets

(56)         References Cited

U.S. PATENT DOCUMENTS

| | | | | |
|---|---|---|---|---|
| 2019/0046121 A1* | 2/2019 | Khachaturian | .... | A61B 5/02055 |
| 2020/0350072 A1* | 11/2020 | McEwing | .............. | G16H 50/70 |
| 2021/0146161 A1* | 5/2021 | Sintay | .................... | G16H 40/20 |
| 2021/0257065 A1 | 8/2021 | Ropa | | |

FOREIGN PATENT DOCUMENTS

| | | | | |
|---|---|---|---|---|
| JP | 2009082498 A | 4/2009 | | |
| KR | 20170120289 A | 10/2017 | | |
| WO | WO-2008130380 A2 * | 10/2008 | ........... | A61B 6/5294 |

OTHER PUBLICATIONS

Taylor, D., "Tableau Architecture & Server Components," Guru99 Website, Available Online at https://www.guru99.com/tableau-architecture.html, Available as Early as Aug. 20, 2022, 6 pages.
Grimes, J. et al., "Pathling: analytics on FHIR," Journal of Biomedical Semantics, vol. 13, No. 23, Sep. 8, 2022, 19 pages.
"Tableau Platform Architecture," Tableau Website, Available Online at https://help.tableau.com/current/blueprint/fr-fr/pp_server_architecture. htm, Retrieved on Oct. 3, 2022, 4 pages.
"Web Data Connector," Tableau Website, Available Online at https://help.tableau.com/current/pro/desktop/en-us/examples_web_data_connector.htm, Retrieved on Oct. 3, 2022, 7 pages.
"Radiation Dose Summary for Diagnostic Procedures on FHIR," HL7 FHIR Website, Available Online at https://build.fhir.org/ig/ HL7/fhir-radiation-dose-summary-ig/background.html, Retrieved on Oct. 3, 2022, 7 pages.
"Adoption of FHIR Standard for Data Interoperability" Tableau Website, Available Online at https://www.tableau.com/learn/webinars/ adoption-fhir-standard-data-interoperability, Retrieved on Oct. 26, 2022, 4 pages.
Anonymous: "Flat-file database", Wikipedia, Sep. 9, 2022 (Sep. 9, 2022), pp. 1-4, XP093132659, Retrieved from the Internet: URL:https:// en.,wikipedia.org/w/index.php?title=Flat-file_database&oldid= 1109393081 [retrieved on Feb. 19, 2024].
CN110008173 Translation of Abstract, Espacenet Search Result Jun. 12, 2024; 1 page.
EP application 23201688.1 filed Oct. 4, 2023—Search report issued Mar. 7, 2024; 18 pages.
JP2009082498 Translation of Abstract, Espacenet Search Result Jun. 12, 2024; 1 page.
Kim Jungsu et al: "Real-Time Patient Radiation Dose Monitoring System Used in a Large University Hospital", Jouirnal of Digital Imaging, Springer International Publishing, Springer International Publishing, Cham, vol. 29, No. 5, Apr. 25, 2016 (Apr. 25, 2016), pp. 627-634, XP036055289, ISSN: 0897-1889, DOI: 10.1007/S10278-016-9880-2 [retrieved on Apr. 25, 2016].
KR1020170120289 Transmission of Abstract, Espacenet Search Result Jun. 12, 2024; 1 page.
Medical Imaging & Technology Alliance: "DICOM PS3.6 2019e—Part 6: Data Dictionary", Dec. 31, 2019 (Dec. 31, 2019), pp. 1-248, XP055897186, Retrieved from the Internet URL: https://web.archive. org/web/20191231115551if_/http://dicom.nema.org/medical/dicom/ current/output/pdf/part06.pdf [retrieved on Mar. 3, 2022].

* cited by examiner

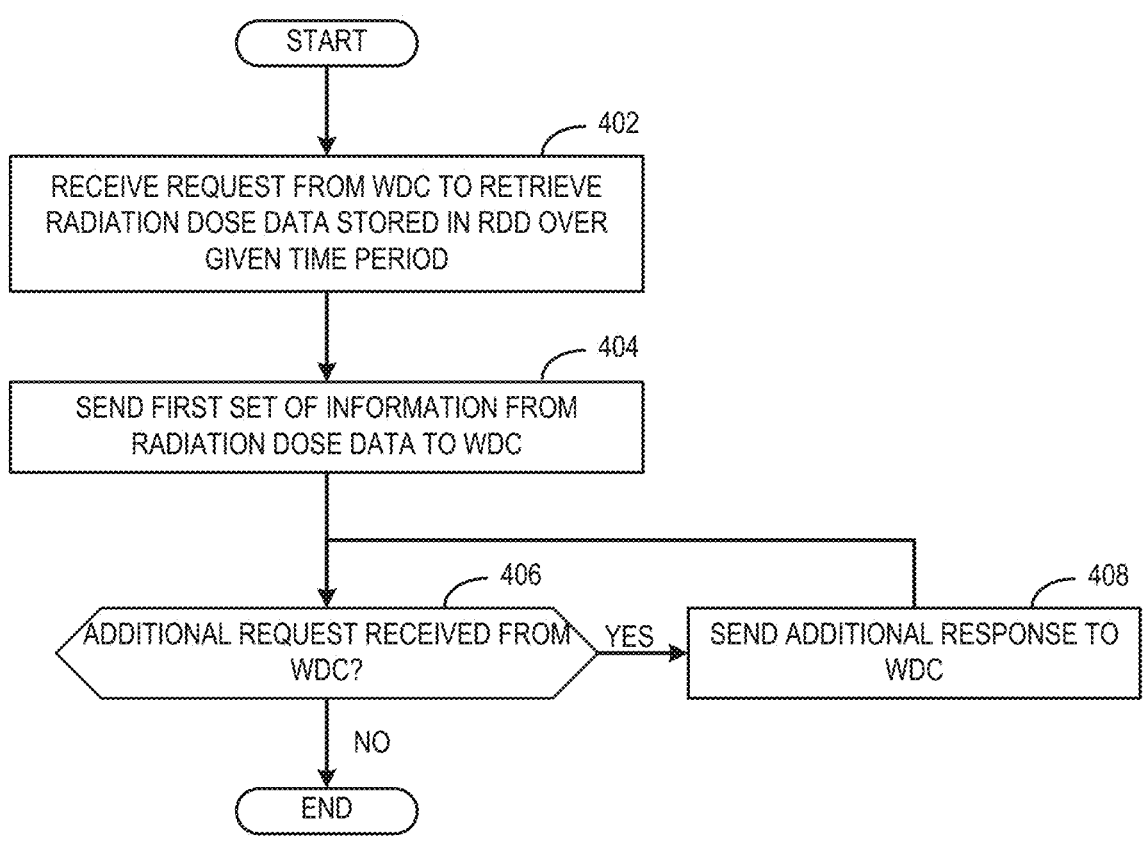
FIG. 4

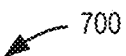
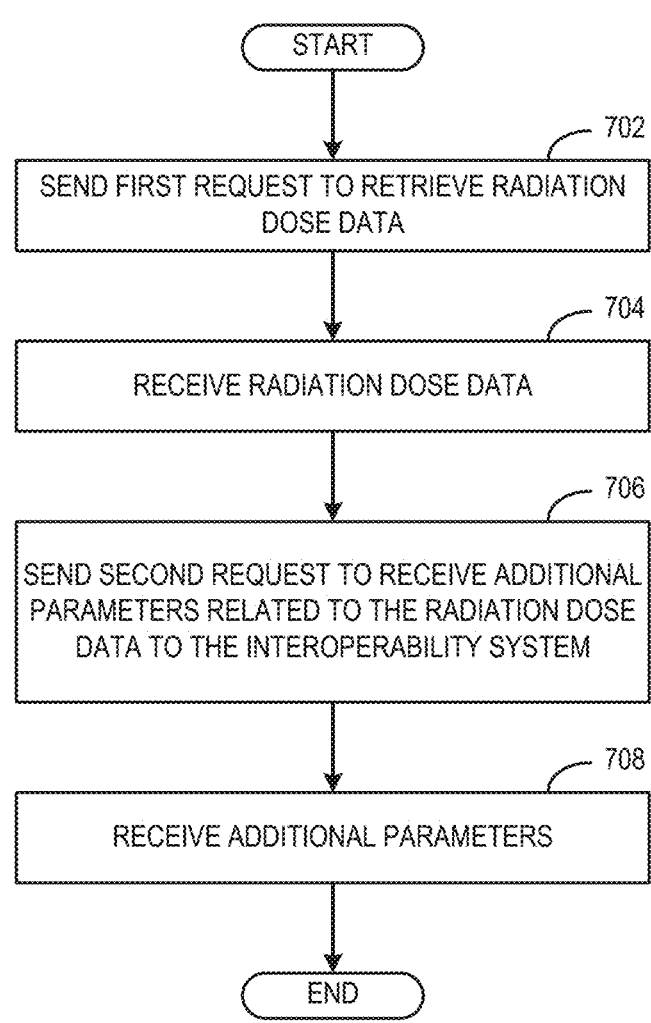
FIG. 7

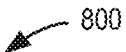
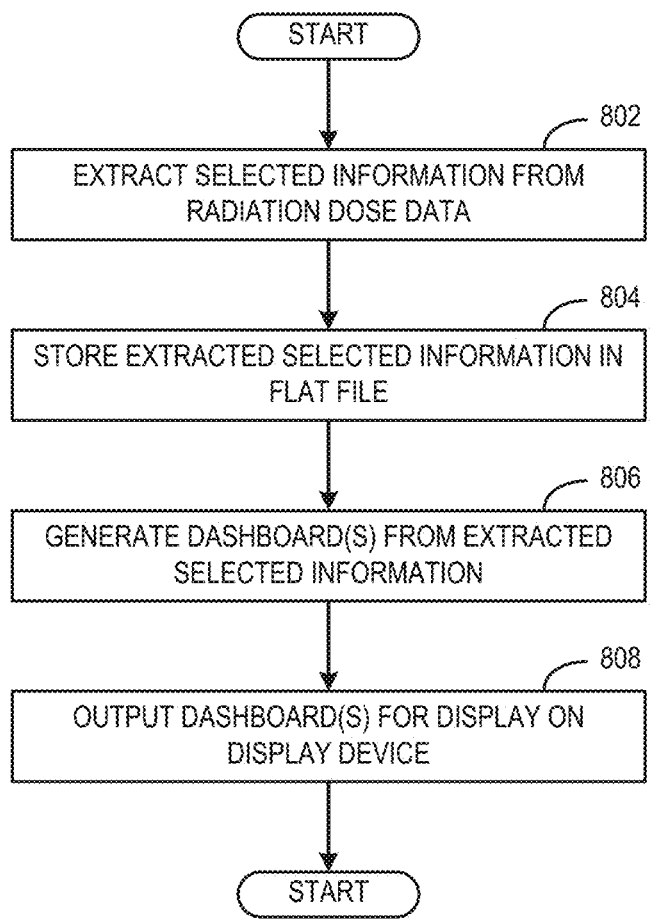
FIG. 8

900

| Metric name | Modality | Unit |
|---|---|---|
| Total DLP | CT | mGy.cm |
| Max CTDIvol | CT | mGy |
| Total DAP | X-Ray | mGy.cm2 |
| Fluoro Total DAP | X-Ray | mGy.cm2 |
| Acquisition Total DAP | X-Ray | mGy.cm2 |
| Total Fluoro Time | X-Ray | s |
| Administered activity | NM | MBq |
| Radiopharmaceutical Volume | NM | cm3 |
| Accumulated Average Glandular Dose | MG | mGy |

| Cohort | CT | X-Ray | MG | NM |
|---|---|---|---|---|
| Device | X | X | X | X |
| Manufacturer | X | X | X | X |
| Model | X | X | X | X |
| Study Description | X | X | X | X |
| Anatomical Region | X | X | | |
| Performing Physician | X | X | X | X |
| Patient Sex | X | X | X | X |
| Patient Weight Range | X | X | X | X |
| Patient BMI Range | X | X | X | X |
| Radiopharmaceutical Agent | | | | X |
| Radionuclide | | | | X |
| Route of administration | | | | X |

FIG. 9B

SYSTEMS AND METHODS FOR MEDICAL DATA TRANSMISSION USING AN AGNOSTIC APPLICATION PROGRAMMING INTERFACE

FIELD

Examples of the subject matter disclosed herein relate to radiation analytics through agnostic transmission of medical data.

BACKGROUND

Third-party tools used to analyze, transform, and/or display medical data collected by an imaging device are largely based on collection of radiation information directly from a database of a radiation management system. However, third-party tools may be configured to interact solely with radiation management systems and databases thereof which use a certain format for data configuration. For example, third-party tools for radiation information may be coupled to a specific provider of a radiation management system. When third-party tools are configured by a manufacturer of the radiation management system to enable direct communication therebetween, operation of the third-party tools may be exclusive to the radiation management system, which may lead to delays and/or cumbersome processes when the radiation management system is updated.

BRIEF DESCRIPTION

In one example, a system for radiation analytics through agnostic transmission of medical data is comprised of memory storing instructions executable by a processor to retrieve radiation dose data in a first format from a radiation dose database via an interoperability system operably coupled to the radiation dose database, convert the radiation dose data to a second format usable by a radiation dose consumer, and generate visualizations of the radiation dose data for display on a display device.

In another example, a system is comprised of a radiation dose database communicably coupled to a plurality of imaging devices, a processor, and memory storing instructions executable by the processor. Based on the executable instructions, the processor may receive requests to send radiation dose data and additional related parameters to a radiation dose consumer. In response to the requests, the system may retrieve the radiation dose data and additional parameters from the radiation dose database and send to the radiation dose consumer. The radiation dose data and the additional related parameters may be formatted according to a Fast Healthcare Interoperability Resources (FHIR®) standard.

In a further example, a system is comprised of a radiation dose database communicatively coupled to a plurality of imaging devices, an interoperability system operatively coupled to the radiation dose database, and a radiation dose consumer communicatively coupled to the interoperability system. The interoperability system is configured to retrieve radiation dose data from the radiation dose database and send the radiation dose data to the radiation dose consumer. The radiation dose data may be formatted according to a Fast Healthcare Interoperability Resources (FHIR®) standard, and the radiation dose consumer is configured to extract selected information from the radiation dose data, store the extracted selected information in a flat file, and generate one or more dashboards from the extracted selected information for display on a display device.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting examples, with reference to the attached drawings, wherein below:

FIG. 4 is a flow chart illustrating an example method for the first example of radiation dose data transmission, from the perspective of an interoperability system;

FIG. 7 is a flow chart illustrating an example method for the second example of radiation dose data transmission, from the perspective of a web data connector;

FIG. 8 is a flow chart illustrating an example method for a second example of radiation dose data transmission, from the perspective of a radiation dose consumer;

FIG. 9A is a first example table illustrating metrics of radiation dose data;

FIG. 9B is a second example table illustrating cohort levels;

DETAILED DESCRIPTION

Figure 1:
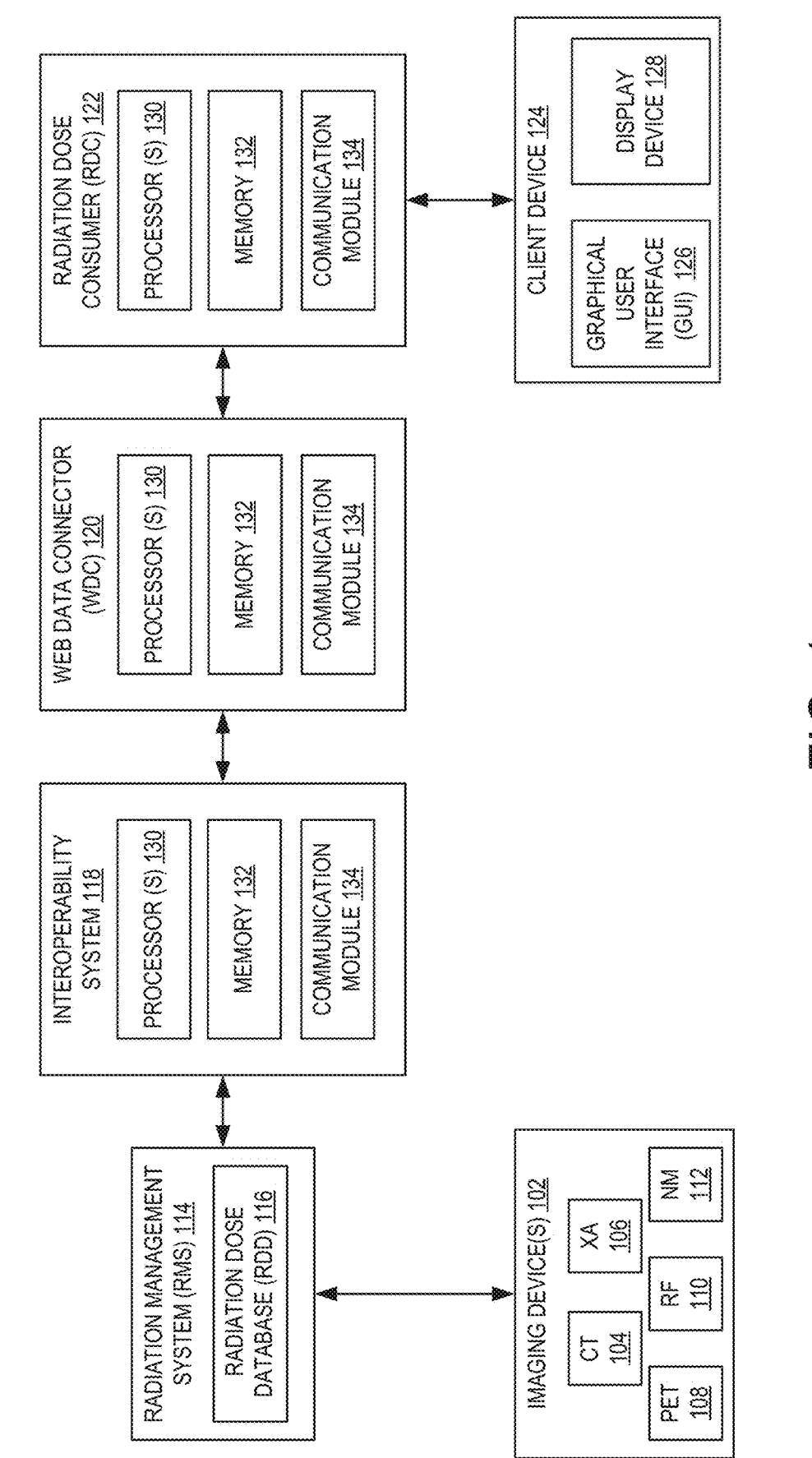
FIG. 1 shows a schematic block diagram of an example system for medical data transmission.

Medical data, such as radiation dose data, may be stored in a format which is characteristic of a system on which the medical data is stored. For example, radiation dose data may be stored on a database of a radiation dose management system in a format characteristic of the radiation dose management system. Third-party tools used to analyze, transform, and/or display radiation dose data may be configured to interact with a specific provider of a radiation dose management system to enable communication therebetween.

For security and/or privacy reasons, third-party tools may not be configured to directly extract data from the database of the radiation dose management system in the format in which the data is stored. Therefore, third-party tools must be specifically configured to acquire data from the radiation dose management system. It may be expensive and/or time consuming to establish a connection between a third-party tool and a radiation dose management system. For example, a third-party tool may be configured to connect to a specific provider of a database (e.g., configured specifically for each radiation dose management system). Operation of a third-party tool may therefore be exclusive to the radiation dose management system to which the third-party tool is communicably coupled and/or configured to, which may lead to delays when the radiation dose management system is updated. For example, any time updates are made to the database of the radiation dose management system, such as nomenclature changes, data model changes, changes to where the data is stored, and so on, the third-party tool must also be updated. For example, a configuration of the third-party tool may be updated to allow communication with an updated radiation dose management system. Configuring the third-party tool to a specific radiation dose management system, as well as updating the third-party tool when the radiation dose management system is updated, may be time and resource consuming. This may also cause delays in acquisition of the data by the third-party, as trained personnel may be used to make the updates.

Delays in data acquisition by third-party tools may create challenges in healthcare settings, as doctors, hospital staff, and regulators rely on data visualizations generated by third-party tools to make decisions about radiation dose delivery to patients. If visualization of radiation dose data is delayed even by a day, up-to-date radiation dose data may not be used in determinations of possible risks to the patients, such as from exceeding a desired maximum amount of radiation administered to a patient. A doctor may inadvertently administer too much radiation to a patient, or a machine emitting excess radiation may not be flagged as needing attention. Disclosed herein are systems and methods which provide a technical benefit of reducing processing and memory demands of the third-party tool, as the third-party tool is enabled by inclusion of a web data connector to connect to any database without database-specific configuration.

FIG. 1 shows a block diagram illustrating a system 100 for medical data transmission and analytics. The system 100 may be used to transmit medical data collected by a hospital modality and stored in a medical database to a third-party analytics tool. In the examples described herein, medical data which is transmitted by the medical data transmission system may be related to a radiation procedure performed by hospital modalities such as imaging systems, however the methods and systems described herein may also be applied for other types of medical data collected by other modalities. Briefly, as described herein, a web data connector (WDC) may be configured to retrieve radiation dose data in a first format from a radiation dose database (RDD) via an interoperability system operably coupled to the RDD and the WDC. The WDC may convert radiation dose data to a second format which is usable by a radiation dose consumer (RDC) operably coupled to the WDC. The RDC may receive radiation dose data in the second format from the WDC, extract selected information from the radiation dose data, and generate visualizations of the radiation dose data for display on a display device. In some examples, the WDC may be integrated in the RDC and the RDC may transform radiation dose data received in the first format via the WDC to the second format. In this way, radiation dose data may be transformed to a standardized format, allowing agnostic transmission of radiation dose data among elements of a system for medical data transmission which may or may not be configured to use an initial format (e.g., the first format) in which radiation dose data is stored.

An imaging device 102 may be a hospital modality, such as a computed tomography (CT) system 104, an x-ray angiography (XA) system 106, a position emission tomography (PET) system 108, a radio fluoroscopy (RF) system 110, and a nuclear medicine (NM) system 112. The imaging device 102 may perform imaging procedures, such as radiation observations in which a patient is exposed to a radiation dose. The imaging device 102 may share data collected by a respective modality to a storage device via at least one of multiple connectivity methods. The multiple connectivity methods may include DICOM® images, DICOM® SRs, HL7®, proprietary logs associated with a manufacturer or operating system, and so on. The imaging device 102 may be operably coupled to a medical database via a wired connection, a wireless connection, and/or any method for communicably connecting systems. As described herein "operably coupled" is to be understood as coupling of elements via connectivity methods (e.g., wired connection, wireless connection, and so on) which enable transfer of data, signals, requests, and/or other information among the operably coupled elements.

In the example described herein, the medical database to which the imaging device 102 is operably coupled is a radiation dose database (RDD) 116 of a radiation dose management system (RMS) 114. The RDD 116 is configured to receive radiation dose data from at least one imaging device 102 and store the radiation dose data. The RDD 116 may be an external database or a local database (e.g., housed on a device of the system 100). The RDD 116 may be a database stored in a mass storage device configured to communicate with secure channels (e.g., HTTPS and TLS), and store data in encrypted form. As further described with respect to FIGS. 2-8, the imaging device 102 may share radiation dose data to the RMS 114, and the RMS 114 may enrich the RDD 116 with data collected from exams performed by the respective hospital modality (e.g., radiation dose data), as well as other exam and/or hospital modality data (e.g., hospital modality manufacturer, hospital modality operator, and so on). The RMS 114 may be further configured with instructions stored on memory and executable by a processor to enable tracking of radiation doses received by a patient over time.

The RMS 114, and specifically the RDD 116, is operably coupled to an interoperability system 118 configured to enable communication between the RMS 114 and third-party analytics tools to allow transfer of radiation dose data therebetween. Briefly, the interoperability system 118 is configured to retrieve radiation dose data from the RDD 116 and send the radiation dose data to a third-party analytics tool. The radiation dose data may include a summary of an imaging procedure, radiation dose administered to a patient, and so on. In some examples, the interoperability system 118 may be integrated in the RMS 114. As further described herein, a summary of radiation procedures related to a specific patient may be shared with third-parties from the RMS 114 using standardized resources defined by the interoperability system 118. This may assist third-parties in easily integrating radiation dose data into their respective applications without use of an interpreter, such as a DICOM® interpreter, for example. The RMS 114 may be configured to expose defined resources, thus exposing radiation dose data through the interoperability system 118, where the interoperability system 118 may enhance third-party usage of data.

In the examples described herein, the interoperability system 118 is configured as a Fast Healthcare Interoperability Resources (FHIR®) application programming interface (API), such that metrics of the interoperability system 118 are provided by the FHIR® API and the radiation dose data is formatted according to a FHIR® standard. Further detail regarding retrieval and transmission of radiation dose data is described with respect to FIGS. 2-10. FHIR® API is a standard for healthcare data exchange, published by HL7®, and defines a plurality of mechanisms used to exchange data continuously without losing or misinterpreting a meaning of the data during transmission between stakeholders. The FHIR® API may enable sharing of a summary of radiation procedures related to a specific patient using standardized FHIR® resources. This may assist third-parties in easily integrating data of the summary of radiation procedures into third-party applications without use of a DICOM® interpreter. Collectively, the plurality of resources defined by the FHIR® API are referred to herein as "radiation dose data" or a "radiation dose summary".

The RMS 114 may be configured to receive and store radiation dose data from at least one imaging device 102. Additionally, as the RMS 114 is operably coupled to and/or integrated with interoperability system 118, the RMS 114 may be configured to operate with the plurality of resources within radiation dose data, as described with respect to the FHIR® API. For example, the RMS 114 may be configured to implement resources including: a CT radiation dose summary, an X-ray radiation dose summary, a radiopharmaceutical radiation dose summary, a CT irradiation event summary, a practitioner, a modality device, an imaging study, and a patient. Other additional or alternative resources may be included, such as patient body mass index (BMI) and patient weight observation. In some examples, the interoperability system 118 may be configured to collect radiation information following requests of the consuming applications. Radiation information may be distributed among different resources of the interoperability system 118.

The interoperability system 118 is further operably coupled to a third-party analytics tool (e.g., a radiation dose consumer (RDC) 122, further described herein) via a web data connector (WDC) 120. The WDC 120 is configured to retrieve the radiation dose data from the RDD 116 via the interoperability system 118 and convert the radiation dose data to a format usable by a third-party tool. The WDC 120 may be configured as a JavaScript script integrated in the RDC 122, in some examples, which may enable the WDC 120 to periodically access the interoperability system 118 (e.g., the FHIR® API) to access different FHIR® resources and use the resources to fill flat file tables. Described another way, the WDC 120 may perform a JavaScript extraction of radiation dose data from the interoperability system 118, following a method described herein. When the interoperability system 118 is configured as the FHIR® API, the WDC 120 may use multiple techniques, such as FHIR® Cast, daily query to the FHIR® API, filtering a plurality of radiation dose data related to a prior query period, and so on to perpetually index and aggregate data from the interoperability system 118.

As briefly described above, the radiation dose data retrieved by the interoperability system 118 from the RDD 116 may be formatted according to a first format (e.g., according to the FHIR® standard of the FHIR® API).

Radiation dose data may be collected (e.g., by the imaging device 102) in a format characteristic of the respective imaging system, and may be converted to the first format prior to transmission from the hospital modality to the RDD 116, in some examples. Alternatively, the radiation dose data may be converted to the first format when the radiation dose data is received by the RDD 116. In further examples, the radiation dose data may be collected by a respective imaging system in the first format. For example, the WDC 120 may enable extraction of radiation dose data from the interoperability system 118 and transformation of radiation dose data into tables (e.g., flat files). The transformed data may be used by a third-party tool which may not be configured to use data having the first format.

As described herein, the third-party tool is the radiation dose consumer (RDC) 122 configured to use defined resources (e.g., radiation dose data) for macroscopic analysis of radiation dose data. This may be used for comparison between devices, cohorts of patients, or comparison between hospitals regarding national radiation dose levels, for example. For example, the RDC 122 may be configured to enable visualization, analysis, analytics, and transformation of data. Data may be collected from multiple sources and aggregated and presented for query and analysis. In FIG. 1, the RDC 122 and the WDC 120 are shown as separate components, however the WDC 120 may be implemented on the RDC 122. In examples where the WDC 120 is implemented on the RDC 122, instructions for obtaining radiation dose data from the RDD 116 and converting the radiation dose data from the first format to the second format, as further described herein with respect to FIGS. 2-8, may be stored as part of the RDC 122. Alternatively, the instructions may be stored on a separate device, such as a server coupled to the RDC 122 via a network. The RDC 122 may be communicably coupled to the WDC 120 through a periodic or perpetual connection. For example, radiation dose data may be retrieved at a set frequency, such as hourly, daily, weekly, and so on. The RDC 122 may enable creation of dashboards based on collected data, which allow users to select metrics and cohort levels to aggregate data in selected cohorts and groups, providing a macroscopic view of the data for analysis, such as detection of anomalies. The RDC 122 may extract selected information from the radiation dose data, store the extracted selected information in a second format, and generate one or more dashboards from the extracted selected information. The second format is the format usable by the third-party tool (e.g., the radiation dose data converted from the first format by the WDC 120) and may be, for example, a flat file. The RDC 122 may identify cohorts in retrieved radiation dose data and enable visualization and/or comparison among cohorts for a same metric.

The RDC 122 is communicably coupled to one or more client devices for display, manipulation, and visualization of analytics on the radiation dose data. Each client device may include a processor, memory, communication module, user input device, display (e.g., screen or monitor), and/or other subsystems and may be in the form of a desktop computing device, a laptop computing device, a tablet, a smart phone, or other device. The client devices may be located locally at the hospital (e.g., as part of hospital administration) and/or remotely from the hospital (such as a user's mobile device). When requested, the dashboard(s) generated by the RDC 122 may be output for display on a display device of a client device as one or more graphical user interfaces. For example, the client device 124 may be configured with a graphical user interface (GUI) 126 and a display device 128. As an example, the client device 124 may store one or more GUI templates in memory that include placeholders for relevant information transmitted to the client device 124 from the RDC 122. For example, the GUI 126 may be configured with a template for a resource dashboard that a user input received by the client device 124 may configure with placeholders for desired patient information. When the GUI 126 is displayed on the client device 124, the relevant information may be retrieved from the RDC 122 (e.g., from a dashboard) and inserted in the placeholders. In other examples, RDC 122 may render selected dashboards into the GUI 126 described herein, and may send the GUI 126 for display on the display device 128 when requested. At least one dashboard generated by the RDC 122 using extracted selected information of the radiation dose data in the second format may be selected using the GUI and selected dashboard(s) may be output for display on the display device. The dashboard(s) may enable visualization of radiation dose data based on cohorts and metrics. The dashboards may not have any specific visual appearance and may include selected radiation dose data aggregated from one or more imaging device 102 and may be updated as new data is received. Further detail regarding dashboard generation and display is described with respect to FIGS. 8-10.

Each of the interoperability system 118, the WDC 120, and the RDC 122 may be configured with resources including a processor 130, a memory 132, and a communication module 134 that may be allocated to store and execute one or more of the methods described herein. Elements of the system 100 may communicate with each other via a network, which may be a suitable wired and/or wireless network. One or more of the devices described herein may be implemented over a cloud or other computer network. Communication module 134 facilitates transmission of electronic data within and/or among one or more systems. Communication via communication module 134 can be implemented using one or more protocols. In some examples, communication via communication module 134 occurs according to one or more standards (e.g., Digital Imaging and Communications in Medicine (DICOM®), Health Level Seven (HL7®), ANSI X12N, etc.). Communication module 134 can be a wired interface (e.g., a data bus, a Universal Serial Bus (USB) connection, etc.) and/or a wireless interface (e.g., radio frequency, infrared, near field communication (NFC), etc.). For example, communication module 134 may communicate via wired local area network (LAN), wireless LAN, wide area network (WAN), etc. using any past, present, or future communication protocol (e.g., BLUETOOTH™, USB 2.0, USB 3.0, etc.). Memory 132 includes one or more data storage structures, such as optical memory devices, magnetic memory devices, or solid-state memory devices, for storing programs and routines executed by processor(s) 130 to carry out various functionalities disclosed herein. Memory 132 may include any desired type of volatile and/or non-volatile memory such as, for example, static random access memory (SRAM), dynamic random access memory (DRAM), flash memory, read-only memory (ROM), etc. Processor(s) 130 may be any suitable processor, processing unit, or microprocessor, for example. Processor(s) 130 may be a multi-processor system, and, thus, may include one or more additional processors that are identical or similar to each other and that are communicatively coupled via an interconnection bus.

As used herein, the terms "sensor," "system," "unit," or "module" may include a hardware and/or software system that operates to perform one or more functions. For example, a sensor, module, unit, or system may include a computer processor, controller, or other logic-based device that per-forms operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

Figure 2:
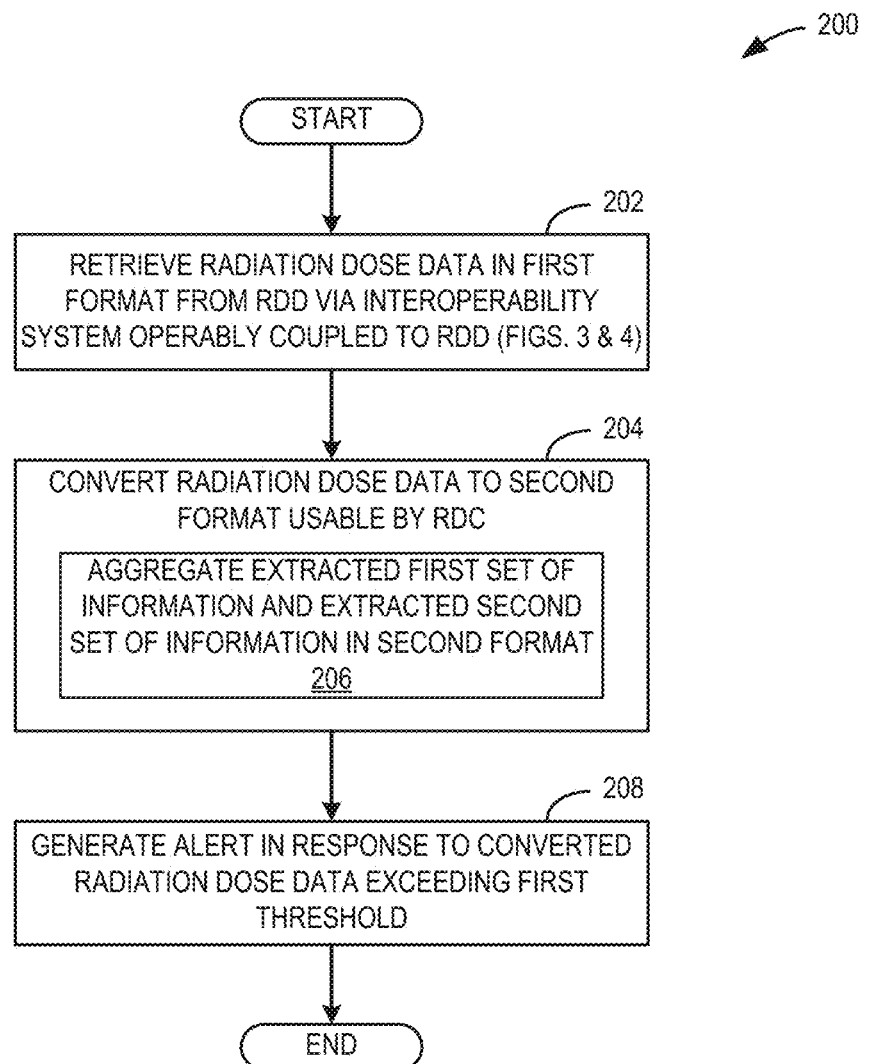
FIG. 2 is a flow chart illustrating an example high-level method for a first example of radiation dose data transmission, from the perspective of a web data connector.
Figure 3:
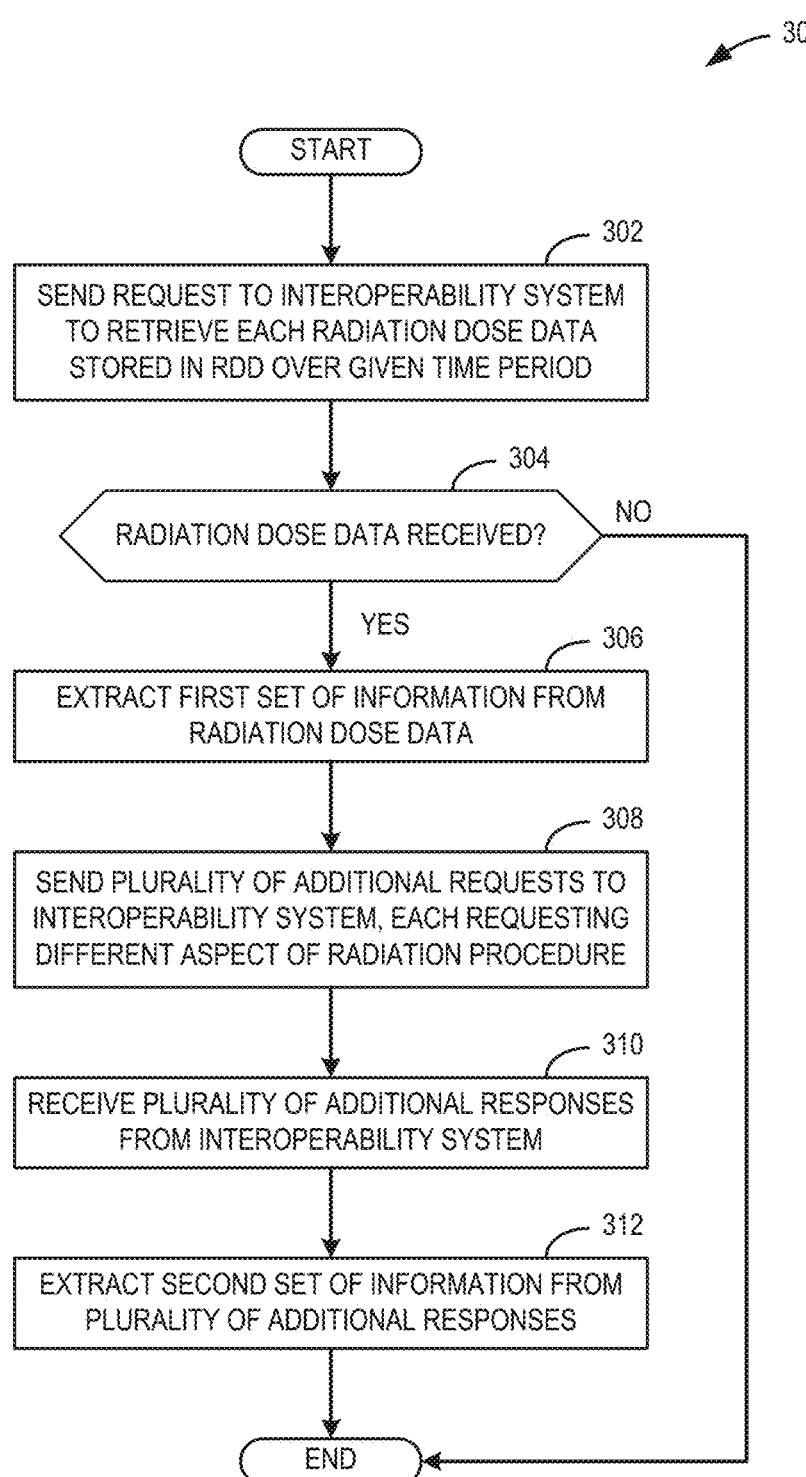
FIG. 3 is a flow chart illustrating an example method for the first example of radiation dose data transmission, from the perspective of the web data connector.

A first example of methods for radiation dose data transmission is described with respect to FIGS. 2-4. The methods of FIGS. 2-4 may be implemented by the system 100 of FIG. 1 and are described with respect thereto. Briefly, the first example of methods for radiation dose data transmission includes retrieval of radiation dose data and additional related parameters from the RDD in a first format by the WDC via the interoperability system, and conversion of the radiation dose data and additional related parameters from the first format to the second format by the WDC. Methods for the first example from the perspective of the WDC are described with respect to FIGS. 2 and 3, and a method from the perspective of the interoperability system is described with respect to FIG. 4.

FIG. 2 is a flow chart illustrating a method 200 for radiation dose data transmission from the perspective of the WDC 120. Thus, the method 200 is carried out according to non-transitory instructions stored in memory of the WDC, such as instructions stored in the memory 132 of the WDC 120. Briefly, radiation dose data transmission includes retrieval of radiation dose data by the WDC from the RDD via the interoperability system. The WDC may send requests to the interoperability system to retrieve radiation dose data, and the interoperability system may respond to the requests by retrieving radiation dose data from the RDD and sending information of the radiation dose data to the WDC. Further detail regarding retrieval of radiation dose data by the WDC is described with respect to FIG. 3 and further detail regarding response of the interoperability system is described with respect to FIG. 4.

At 202, the method 200 includes retrieving radiation dose data in a first format from the RDD via the interoperability system operably coupled to the RDD. As described above, the radiation dose data may be stored in the RDD in the first format, where the first format may format the radiation dose data according to the FHIR® standard of the FHIR® API. For example, the first format may comprise a JavaScript object (JSON). Further detail regarding retrieval of radiation dose data is described with respect to FIGS. 3 and 4.

At 204, the method 200 includes converting radiation dose data from the first format to a second format which is usable by the RDC. As described above, the RDC may be configured to process data having the second format, where the second format is different from the first format which is used by the RDD. For example, the second format may configure the radiation dose data as flat files. The RDC and the RDD may have different manufacturers, operators, developers, and so on for which use of different data formats are desired. As further described with respect to FIG. 8, converting the radiation dose data from the first format to the second format may enable use of the data by the RDC, regardless of the initial storage format of the radiation dose data (e.g., the first format).

Operation 204 further includes aggregating an extracted first set of information and an extracted second set of information in the second format at 206. As further described with respect to FIG. 3, extraction of a first set of information and a second set of information may include selecting data of interest from the radiation dose data, stripping the selected data of interest of the first format, and reformatting the selected data of interest in the second format. The first set of information and the second set of information, configured in the second format, may be aggregated to provide to the RDC a desired selection of radiation dose data in the second format.

The method 200 may further include, at 208, generating an alert in response to converted radiation dose data exceeding a first threshold. For example, and as further described with respect to FIGS. 9-12, the converted radiation dose data may include a total dose length product (DLP), indicating a measure of CT tube radiation exposure of a subject. The first threshold is a recommended maximum amount of radiation exposure for the subject's weight, age, sex, etc., beyond which the subject may experience undesired radiation effects. When the total DLP exceeds a first threshold, the method 200 may include generating an alert. The alert may be configured as a sound, a visual, or another configuration which alerts a system and/or a user to an exceeded first threshold. For example, the alert may be output for display on a display device (e.g., display device 128 of FIG. 1). The alert may be output at the time of generation, in some examples. In other examples, the alert may be integrated into the aggregated radiation dose data, such that when the radiation dose data is called up, for example, when generating a dashboard as described with respect to FIGS. 8-12, the alert is output. In some examples, any of the devices in the system 100 for medical data transmission, including the RDC 122, the WDC 120, the interoperability system 118, the client device 124, and/or the RMS 114 may generate an alert that is transmitted to a user when a radiation dose (e.g., a metric of the radiation dose data) reaches a respective threshold, where the respective threshold indicates a radiation dose at or above which is an undesirable dose for patient exposure.

In some examples, the WDC may transmit the converted and aggregated radiation dose data to a separate device. For example, the converted and aggregated radiation dose data may be transmitted from the WDC to another storage device, database, and/or system configured to use radiation dose data in the second format. The method 200 ends. An example describing operation of the WDC in further detail is described with respect to FIGS. 10A and 10B.

FIG. 3 is a flow chart illustrating a method 300 for radiation dose data transmission from the perspective of the WDC 120 and includes further detail of operation 202 of the method 200. Specifically, the method 300 illustrates request, receipt, and extraction of radiation dose data. In this way, the WDC may acquire radiation dose data from the RDD via the interoperability system and extract information sets from the radiation dose data to convert information from the first format to the second format, where the second format is usable by the RDC. The method 300 is carried out according to non-transitory instructions stored in memory of the WDC, such as instructions stored in the memory 132 of the WDC 120.

At 302, the method 300 includes sending a request to the interoperability system to retrieve radiation dose data stored in the RDD over a given time period. The request may indicate desired retrieval of a plurality of radiation dose data for a plurality of patients and/or a plurality of imaging procedures within the given time period. For example, the given time period may be one hour, six hours, twelve hours, twenty-four hours, and so on, for example. In this way, the WDC may request that the interoperability system retrieve a plurality of radiation dose data on an hourly, daily, or weekly basis. The request may be designed to request the latest radiation dose data (e.g., since a prior request) and not a complete history of radiation stored on the RDD. The WDC may request that the interoperability system collects data: related to a related irradiating device, related to the performed exam type (e.g., imaging procedure type), related to a cohort of irradiated patients, and, based on the imaging procedure reported by the imaging procedure, collects data and metrics related to the CT, X-ray, MAMMO, or NM procedure.

At 304, the method 300 includes determining if radiation dose data is received. Radiation dose data may not be received when, for example, no imaging procedures are performed since a previous request for radiation dose data retrieval. Additionally or alternatively, radiation dose data may not be retrieved when no additional radiation dose data have been stored in the RDD since a previous request for radiation dose data retrieval. If radiation dose data is not received, the method 300 ends.

If radiation dose data is received at 304, the method 300 proceeds to 306, where the method 300 includes extracting a first set of information from the radiation dose data. The first set of information may be comprised of an identification of the radiation dose data (e.g., a numerical identifier, a name, and so on), a date and a time at which the imaging procedure to collect the radiation dose data commenced, and a radiation procedure used to collect the radiation dose data. The first set of information may further be comprised of one or more modality-specific (e.g., hospital modality-specific) radiation dose metrics. In some examples, extracting the first set of information may further comprise stripping data of the first set of information of the first format (e.g., configured as JSON).

At 308, the method 300 includes sending a plurality of additional requests to the interoperability system, where each request of the plurality of additional requests is requesting information related to a different aspect of the radiation procedure (e.g., identified in the first set of information). For example, the plurality of additional requests may request information including parameters of a device used to carry out the radiation procedure, an imaging study description of the radiation procedure, patient information of a patient imaged via the radiation procedure, and performer information of a clinician who authorized and/or oversaw the radiation procedure. At 310, the method 300 includes receiving a plurality of additional responses from the interoperability system, where the plurality of additional responses corresponds with the plurality of additional requests sent at operation 308.

At 312, the method 300 includes extracting a second set of information from the plurality of additional responses. Similar to operation 306, extracting the second set of information may include stripping data of the plurality of additional request of the first format (e.g., configured as JSON). Method 300 ends.

Returning briefly to the method 200 of FIG. 2, the first set of information and the second set of information extracted as described with respect to the method 300 may be converted to the second format at operation 204 (e.g., condensed into flat files). The first set of information and the second set of information may then be aggregated into a single dataset in the second format at operation 206. As further described with respect to FIGS. 5 and 8-11, the aggregated first and second set of information in the second format may be used by the RDC to generate at least one dashboard for comparison of metrics and cohorts of the radiation dose data.

As described above with respect to FIG. 2, the WDC retrieves radiation dose data from the RDD via the interoperability system operably coupled to the RDD and the WDC. FIG. 4 is a flow chart illustrating a method 400 for radiation dose data transmission from the perspective of the interoperability system 118. Briefly, the method for radiation dose data transmission as performed by the interoperability system includes receiving requests to retrieve a plurality of radiation dose data, and sending information of the radiation dose data to the WDC. The method 400 is carried out according to non-transitory instructions stored in memory of the interoperability system, such as instructions stored in the memory 132 of the interoperability system 118.

At 402, the method 400 include receiving a request from the WDC to retrieve radiation dose data stored in the RDD over a given time period (e.g., the request sent at operation 302 of method 300). As described with respect to FIG. 3, the request may indicate desired retrieval of a plurality of radiation dose data for a plurality of patients and/or a plurality of imaging procedures within the given time period. For example, the given time period may be one hour, six hours, twelve hours, twenty-four hours, and so on, for example. In this way, the interoperability system may retrieve a plurality of radiation dose data on an hourly, daily, or weekly basis. The interoperability system may collect data: related to a related irradiating device, related to the performed exam type (e.g., imaging procedure type), related to a cohort of irradiated patients, and, based on the imaging procedure reported by the radiation dose data, collects data and metrics related to the CT, X-ray, MAMMO, or NM procedure.

At 404, the method 400 includes sending a first set of information from radiation dose data to the WDC. Following operations of the method 400 are described with respect to a single set of radiation dose data (e.g., from a single imaging procedure performed on a single patient), however it is to be understood that the first set of information and subsequent additional responses may be collected for each of a number of radiation dose data retrieved from the RDD (e.g., a set of data for each imaging procedure performed on each patient). As described above with respect to FIG. 3, the first set of information may include an identification of the radiation dose data (e.g., a numerical identifier, a name, and so on), a date and a time at which a radiation observation (e.g., imaging procedure) to collect the radiation dose data commenced, and an imaging procedure used to collect the radiation dose data. The first set of information may further be comprised of one or more modality-specific (e.g., hospital modality-specific) radiation dose metrics. The first set of information may be sent to the WDC in the first format (e.g., JSON). A first set of information corresponding to each radiation dose data retrieved from the RDD may be sent to the WDC.

At 406, the method 400 includes determining if an additional request is received from the WDC. The additional request may be a request of the plurality of additional requests sent to the interoperability system at operation 308 of method 300, wherein the plurality of additional requests each request a different aspect of the radiation procedure. If an additional request is not received, the method 400 ends. If an additional request is received at 406, at 408 the method 400 includes sending a corresponding additional response to the WDC. For example, information including parameters of a device used to carry out the radiation procedure, an imaging study description of the radiation procedure, patient information of a patient imaged via the radiation procedure, and performer information of a clinician who authorized and/or oversaw the radiation procedure for given radiation dose data may be retrieved from the RDD and sent to the WDC. An additional request may include information from the first set of information, such as an identification of the radiation dose data, such that information of the additional response corresponds to respective radiation dose data. Method 400 ends.

Returning briefly to FIG. 2 and as described with respect to the method 300, the second set of information may be extracted from the additional parameters received by the WDC from the interoperability system. Some or all of the additional parameters may be extracted to form the second set of information. The first set of information and the second set of information, both stripped of the first format, may be converted to the second format, which is useable by the RDC, and aggregated to form a single dataset. The single dataset may include radiation dose data for a single radiating event (e.g., imaging procedure) for a single patient. Multiple single datasets may be generated according to the methods of FIGS. 2-3, where each of the multiple single datasets represents a single radiating event for a single patient. A patient may have multiple single datasets, each representing radiation dose data for a different imaging procedure. As further described with respect to FIGS. 5-11, single datasets may be compared using a dashboard generated based on the radiation dose data by the RDC. This may enable comparison among imaging devices, imaging procedures, patient characteristics including age, weight, sex, preexisting conditions, and so on, relative to radiation dosage.

Figure 5:
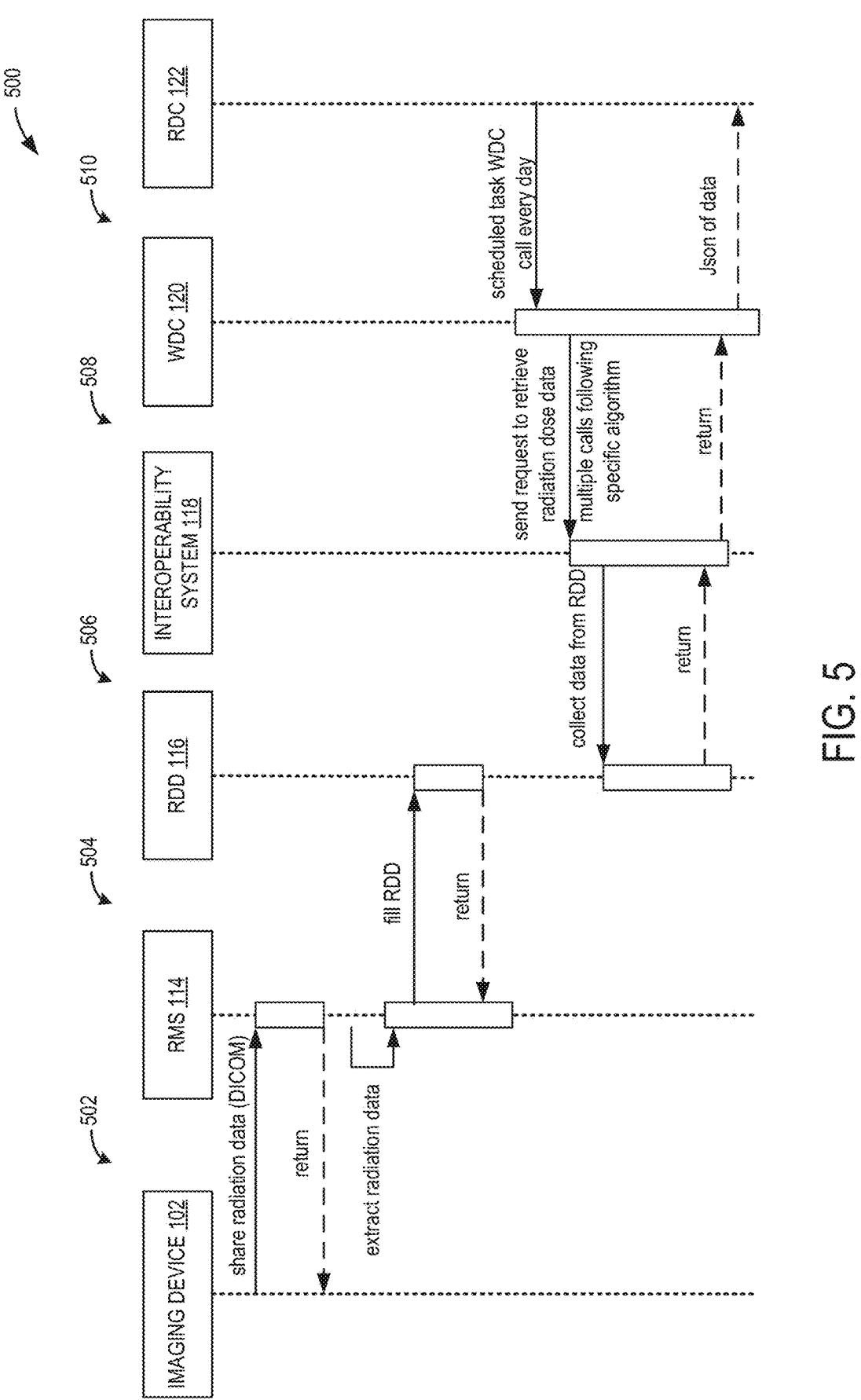
FIG. 5 shows a block diagram illustrating interaction of elements of the example system for medical data transmission of FIG. 1.
Figure 6:
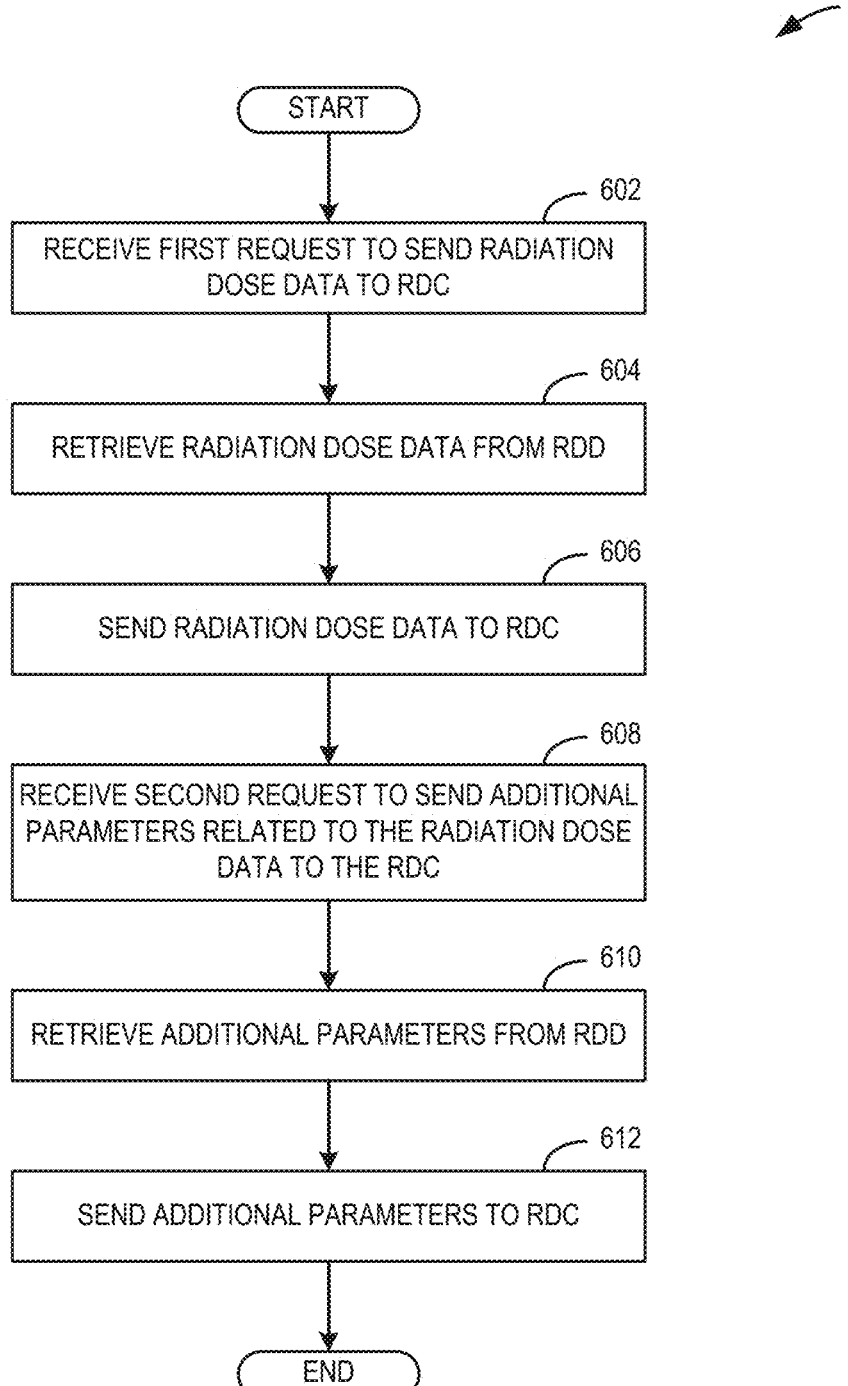
FIG. 6 is a flow chart illustrating an example method for a second example of radiation dose data transmission, from the perspective of an interoperability system.

FIG. 5 shows a timeline 500 illustrating interaction among elements of the system 100 during the first example of radiation dose data transmission, as described with respect to FIGS. 2-4 and a second example of radiation dose data transmission further described with respect to FIGS. 6-8. The imaging device 102 (e.g., the CT system 104, the XA system 106, the PET system 108, the RF system 110, and the NM system 112) may perform an imaging procedure and transmit radiation dose data to the RMS 114 at operation 502. For example, the imaging device 102 may share radiation dose data in a DICOM® format. Transmission of radiation dose data to the RMS 114 may occur at a frequency, such as hourly, daily, or after each imaging procedure, for example. The radiation dose data transmitted to the RMS 114 may include more data than may be desired by a third-party tool for analysis. Additionally or alternatively, the radiation dose data transmitted to the RMS 114 may be transmitted as a single unit or file.

The RMS 114 may extract radiation dose data from radiation dose data transmitted to the RMS by the imaging device 102. Extracting radiation dose data may include parsing out individual data types from the radiation dose data. Extracted radiation dose data is used to fill the RDD 116 (e.g., of the RMS 114) at operation 504. The RDD 116 may be continuously filled as radiation dose data is extracted by the RMS 114, or the RDD 116 may be filled at a frequency, such as hourly or daily, where extracted data from a plurality of imaging procedures fill the RDD 116 together instead of one at a time, coinciding with when the respective imaging procedure is performed.

As described with respect to methods 300 and 400, the WDC 120 and the interoperability system 118 may operably interact to request and retrieve radiation dose data from the RDD 116. At operation 508, the WDC 120 and the interoperability system 118 may interact to send and receive requests to retrieve a plurality of radiation dose data, respectively, and to send retrieved radiation dose data from the interoperability system 118 to the WDC 120. For example, at 302, the method 300 includes sending a first request to the interoperability system 118 from the WDC 120 and at 402, the method 400 includes the interoperability system 118 receiving the first request from the WDC 120. At operation 506 and as further described with respect to a method 600 of FIG. 6, the interoperability system 118 collects (e.g., retrieves) radiation dose data from the RDD 116. With reference to FIG. 5, the WDC 120 may send multiple calls (e.g., requests) to the interoperability system 118 to retrieve data, following a specific algorithm. For example, as described with respect to methods 300 and 400, at 308 of method 300, the WDC 120 may send a plurality of additional requests to the interoperability system 118 and at 406 of method 400, the interoperability system 118 may receive at least one additional request from the WDC 120. Additionally, the WDC 120 may send the first request and the plurality of additional requests to the interoperability system 118 at a frequency (e.g., hourly, daily, weekly, and so on) to enable retrieval of a plurality of radiation dose data sets, such as from a plurality of patients, a plurality of imaging devices, a plurality of imaging procedures, and so on.

Following retrieval of radiation dose data by the interoperability system 118 from the RDD 116 at operation 506, the radiation dose data may be transmitted to the WDC 120 at operation 508. Further detail regarding retrieval of radiation dose data by the interoperability system is described with respect to FIG. 6. As described with respect to method 300, at 304, the method 300 includes determining if radiation dose data is received and at 310, the method 300 includes receiving a plurality of additional responses from the interoperability system 118. At 404 of method 400, the interoperability system 118 may send a first set of information to the WDC 120 and, at 408, the interoperability system 118 may send additional responses to the WDC 120.

At operation 510, the RDC 122 receives radiation dose data from the WDC 120. The RDC 122 may have a scheduled task (e.g., hourly, daily, weekly, and so on) to call on the WDC 120 to retrieve radiation dose data therefrom. Further detail regarding operation of the RDC 122 is described with respect to FIG. 8. Briefly, in some examples, the RDC 122 may receive radiation dose data from the WDC 120 in a first format. For example, the first format may be JSON. The RDC 122 may convert the radiation dose data from the first format to a second format. For example, the second format may be flat files. In other examples, the WDC 120 may extract radiation dose data and convert the radiation dose data from the first format to the second format (e.g., flat files). The WDC 120 may send radiation dose data in the second format to the RDC 122. When the radiation dose data is in the second format, the RDC 122 may be able to access and use the radiation dose data. For example, the RDC 122 may generate at least one dashboard based on the radiation dose data and output the at least one dashboard for display on a display device. Further detail regarding generation of dashboards based on radiation dose data is described with respect to FIGS. 8-10.

A second example of methods for radiation dose data transmission is described with respect to FIGS. 6-8. The methods of FIGS. 6-8 may be implemented by the system 100 of FIG. 1 and are described with respect thereto. Briefly, the second example of methods for radiation dose data transmission includes retrieval of radiation dose data and additional related parameters from the RDD by the interoperability system, receipt of retrieved radiation dose data and additional related parameters from the interoperability system by the WDC, and extraction and format conversion of a selection of retrieved radiation dose data from the WDC by the RDC. A method for the second example of radiation dose transmission from the perspective of the interoperability system is described with respect to FIG. 6, from the perspective of the WDC is described with respect to FIG. 7, and from the perspective of the RDC is described with respect to FIG. 8.

FIG. 6 is a flow chart illustrating a method 600 for the second example of radiation dose data transmission from the perspective of the interoperability system 118. Briefly, the method 600 includes: receiving requests to send data to the RDC, retrieving data from the RDD, and sending data to the RDC. As further described with respect to FIGS. 7 and 8, the interoperability system may send radiation dose data to the RDC via the WDC, which is operably coupled to and/or integrated within the RDC. The method 600 is carried out according to non-transitory instructions stored in memory of the interoperability system, such as instructions stored in the memory 132 of the interoperability system 118.

At 602, the method 600 includes receiving a first request to send a plurality of radiation dose data to the RDC. The interoperability system may receive the first request from the WDC, as further described with respect to FIG. 7. As described with respect to FIGS. 3-5, the first request may indicate desired retrieval of a plurality of radiation dose data for a plurality of patients and/or a plurality of imaging procedures performed within a given time period. For example, the given time period may be one hour, six hours, twelve hours, twenty-four hours, and so on, for example.

At 604, the method 600 includes retrieving a plurality of radiation dose data from the RDD. As the interoperability system is operably coupled to the RMS, the interoperability system may access the RDD to retrieve radiation dose data. The interoperability system may retrieve a plurality of radiation dose data which have been input into the RDD following a prior retrieval of the plurality of radiation dose data by the interoperability system. The interoperability system may collect data: related to a related irradiating device, related to the performed exam (e.g., imaging procedure), related to the irradiated patient, and, based on the imaging procedure reported by the radiation dose data, collects data and metrics related to the CT, X-ray, MAMMO, or NM procedure.

At 606, the method 600 includes sending the plurality of radiation dose data retrieved at operation 604 to the RDC. Radiation dose data may include an identification of the radiation dose data (e.g., a numerical identifier, a name, and so on), a date and a time at which the radiation observation (e.g., imaging procedure) commenced, and a radiation procedure used to collect the radiation dose data. The radiation dose data information may further be comprised of one or more modality-specific (e.g., hospital modality-specific) radiation dose metrics.

In examples where the WDC is integrated in the RDC, radiation dose data may be sent from the interoperability system to the RDC in the first format (e.g., JSON). The WDC, as an element of the RDC, may receive the plurality of radiation dose data in the first format, as described with respect to FIG. 7, and the RDC may perform conversion of radiation dose data from the first format to the second format, as further described with respect to FIG. 8. In examples where the WDC and the RDC are separate, operably coupled elements, the plurality of radiation dose data may first be sent to the WDC and the RDC may routinely call the WDC (e.g., send a request to retrieve radiation dose data for a given time period) to retrieve and extract desired radiation dose data, as further described with respect to FIGS. 7 and 8.

At 608, the method 600 includes receiving a second request to send additional parameters related to the radiation dose data to the RDC. As further described with respect to FIG. 7, the second request may be sent to the interoperability system by the WDC. The additional request may be a request for a plurality of different aspect of the radiation procedure for radiation dose data retrieved by the interoperability system (e.g., at operation 604). For example, different aspects of the radiation procedure may include parameters of a device used to carry out the radiation procedure, an imaging study description of the radiation procedure, patient information of a patient imaged via the radiation procedure, and performer information of a clinician who authorized and/or oversaw the radiation procedure.

At 610, the method 600 includes retrieving additional parameters from the RDD. The additional parameters to be retrieved are indicated by the second request and correspond with radiation dose data of the at least one radiation dose data retrieved at operation 604.

At 612, the method 600 includes sending corresponding additional response to the RDC. As described with respect to operation 606, additional parameters may be sent from the interoperability system to the RDC in the first format when the WDC is integrated in the RDC. The WDC, as an element of the RDC, may receive the additional parameters in the first format, as described with respect to FIG. 7, and the RDC may perform conversion of the additional parameters from the first format to the second format, as further described with respect to FIG. 8. In examples where the WDC and the RDC are separate, operably coupled elements, additional parameters may first be sent to the WDC and the RDC may routinely call the WDC to retrieve and extract desired radiation dose data, as further described with respect to FIGS. 7 and 8. The method 600 ends.

FIG. 7 is a flow chart illustrating a method 700 for the second example of radiation dose data transmission from the perspective of the WDC 120. As described with respect to method 600 of FIG. 6, the WDC may send requests to the interoperability system to retrieve radiation dose data and additional related parameters (e.g., from the RDD). The WDC also receives retrieved radiation dose data and additional related parameters from the interoperability system as an intermediate between the interoperability system and the RDC. The method 700 is carried out according to non-transitory instructions stored in memory of the interoperability system, such as instructions stored in the memory 132 of the WDC 120.

At 702, the method 700 includes sending a first request to retrieve a plurality of radiation dose data. The first request sent by the WDC is the first request received by the interoperability system, as described with respect to operation 602 of method 600.

At 704, the method 700 includes receiving the plurality of radiation dose data from the interoperability system. The plurality of radiation dose data received by the WDC are the radiation dose data retrieved by the interoperability system from the RDD at operation 604 of method 600. The WDC may receive a plurality of radiation dose data which have been input into the RDD following a prior retrieval of the plurality of radiation dose data by the interoperability system.

At 706, the method 700 includes sending a second request to the interoperability system to receive additional parameters related to the radiation dose data. The second request may be a request for a plurality of different aspect of the radiation procedure for the radiation dose data retrieved by the interoperability system (e.g., at operation 604 of method 600). For example, different aspects of the radiation procedure may include parameters of a device used to carry out the radiation procedure, an imaging study description of the radiation procedure, patient information of a patient imaged via the radiation procedure, and performer information of a clinician who authorized and/or oversaw the radiation procedure.

At 708, the method 700 includes receiving additional parameters. The additional parameters are additional parameters retrieved from the RDD at operation 610 of method 600. At least one additional parameter may be received which corresponds to each of at least one radiation dose data received at operation 704. The method 700 ends.

FIG. 8 is a flow chart illustrating a method 800 for the second example of radiation dose data transmission from the perspective of the RDC 122. As described with respect to method 700 of FIG. 7, the WDC may receive the plurality of radiation dose data and additional parameters related to the radiation dose data from the RDD via the interoperability system. The WDC may be integrated in and/or operably coupled to the RDC, which enables the RDC to access and use the plurality of radiation dose data and related additional parameters received by the WDC from the interoperability system. The RDC is configured to extract selected information from the radiation dose data and related additional parameters, convert extracted selected information from a first format to a second format, and generate one or more dashboards from extracted selected information for display on a display device. The method 800 is carried out according to non-transitory instructions stored in memory of the RDC such as instructions stored in the memory 132 of the RDC 122.

At 802, the method 800 includes extracting selected information from radiation dose data. For example, selected information may include at least one of an identification of the radiation dose data (e.g., a numerical identifier, a name, and so on), a date and a time at which the imaging procedure to collect radiation dose data commenced, a radiation procedure used to collect the radiation dose data, parameters of a device used to carry out the radiation procedure, an imaging study description of the radiation procedure, patient information of a patient imaged via the radiation procedure, and performer information of a clinician who authorized and/or oversaw the radiation procedure. Extracting selected information may include stripping the selected information of the first format. For example, the first format may configure the data according to the FHIR® standard of the FHIR® API (e.g., JSON).

At 804, the method 800 includes storing extracted selected information in a flat file. For example, a second format (e.g., the flat file) may be applied to extracted selected information from the radiation dose data (e.g., as described with respect to operation 802). The RDC 122 may collect raw data (e.g., radiation dose data stripped of the first format), flatten the raw data, and fill tables to form flat files. Metrics used by the RDC 122, as further described with respect to FIGS. 9A and 9B, may be defined in tables CT metrics, X-ray metrics, MAMMO metrics, and NM metrics. Further detail regarding metrics and cohort levels are described with respect to FIGS. 9A and 9B.

At 806, the method 800 includes generating at least one dashboard from extracted selected information. As the extracted selected information has been converted from the first format (e.g., JSON) to the second format (e.g., flat files), the extracted selected information may be stored by the RDC in a format which is useable by the RDC (e.g., the flat files may be read and/or manipulated by instructions of the RDC). Each of the at least one dashboard may be used to compare cohorts and metrics of multiple radiation dose data (e.g., for multiple patients and/or multiple imaging procedures). Further detail regarding generation of dashboards is described with respect to FIGS. 10 and 11. A dashboard may be manually configured to expose the extracted selected information, including collected metrics, as described with respect to FIG. 9A, regarding identified cohorts, as described with respect to FIG. 9B. For example, an analytics tool may be used to configure a dashboard, where the analytics tool allows for configuring a layout of the dashboard, selection of types of dashboards to render, and for each dashboard, selecting rows, columns, and parameters (e.g., colors, sizes, labels, etc.). Following configuration of the dashboard, at least one dashboard may be auto-populated with the extracted selected information to generate the at least one dashboard.

At 808, the method 800 includes outputting the at least one dashboard (e.g., generated at operation 806) for display on a display device. For example, the at least one dashboard may be output to the client device 124 to be displayed on the display device 128. The method 800 ends.

Returning briefly to FIG. 5, interaction among elements of the system 100 as described with respect to the second example of radiation dose data transmission described with respect to FIGS. 6-8 may be visualized in the timeline 500. The WDC 120 and the interoperability system 118 may operably interact to request and retrieve radiation dose data from the RDD 116 at operation 508 and 506, respectively. For example, at 702, the method 700 described from the perspective of the WDC 120 includes sending a first request to the interoperability system 118 and, at 706, includes sending a second request to the interoperability system 118. At 602, the method 600 described from the perspective of the interoperability system 118 includes receiving a first request from the WDC 120 and, at 608, receiving a second request from the WDC 120. Following receipt of the first request and the second request, method 600 includes retrieving radiation dose data at 604 and retrieving additional parameters at 610, respectively, from the RDD (e.g., at operation 506 of FIG. 5).

Following retrieval of radiation dose data by the interoperability system 118 from the RDD 116 at operation 506, the radiation dose data may be transmitted to the WDC 120 at operation 508. At 606, the method 600 includes sending multiple radiation dose data to the RDC 122 via the WDC 120, wherein at 704 of the method 700, the WDC 120 receives multiple radiation dose data retrieved by the interoperability system 118. Similarly, at 612, the method 600 includes sending additional parameters to the RDC 122 via the WDC 120, wherein at 708 of the method 700, the WDC 120 receives additional parameters retrieved by the interoperability system 118.

As described with respect to FIG. 8, the RDC 122 may call the WDC 120 to receive data received by the WDC 120 from the interoperability system 118 at operation 510 of FIG. 5. In some examples, the RDC 122 may receive data formatted according to the first format (e.g., JSON) and may convert data from the first format to the second format. As described with respect to the method 800, at 802, the method 800 includes extracting selected information (e.g., removing the first format) and, at 804, storing extracted selected information in a flat file (e.g., in the second format). The RDC 122 may use data in the second format to generate dashboards from extracted selected information, as further described with respect to FIGS. 10 and 11.

The RDC 122 may provide a range of possible methods for exploiting, analyzing, comparing, and displaying radiation dose data formatted according to the second format. For example, the RDC 122 may generate dynamic views of radiation dose data, such as dashboards, and output the dynamic views for display on a display device, such as the display device 128 of the client device 124 of FIG. 1. Data filters used to select cohorts and metrics of data to be used to generate dashboards may be selected by a user input through interaction with the GUI 126, in some examples. For examples, filters may include selection of a period of time, an imaging system, an imaging procedure, a manufacturer, and so on. In other examples, dashboards and/or other dynamic views of the radiation dose data may be automatically generated by the RDC 122 and a user input may represent a selection of which dashboard to view via interaction with the GUI 126.

Following collection of radiation dose data (e.g., following retrieval of radiation dose data from the RDD 116 by the interoperability system 118) metrics may be made available for use by the RDC 122. For example, information extracted from the radiation dose data and useable as metrics may include: total dose length product (DLP) and max CTDIvol for radiation dose data collected by CT systems; total dose area product (DAP), fluoro total DAP, acquisition total DAP, and total fluoro time for radiation dose data collected by X-ray systems; administered activity and radiopharmaceutical volume for radiation dose data collected by NM systems; and accumulated average glandular dose for radiation dose data collected by MG systems. Units and modalities of example metrics are shown in a first table 900 of FIG. 9A. The RDC 122 may identify cohorts used to sort and/or compare data of the aforementioned metrics. A second table 950 of FIG. 9B shows example cohort levels which may be used for radiation dose data collected by different imaging devices. Multiple cohort levels may be used to analyze and/or compare each metric (e.g., metrics shown in the first table 900).

Figure 10A:
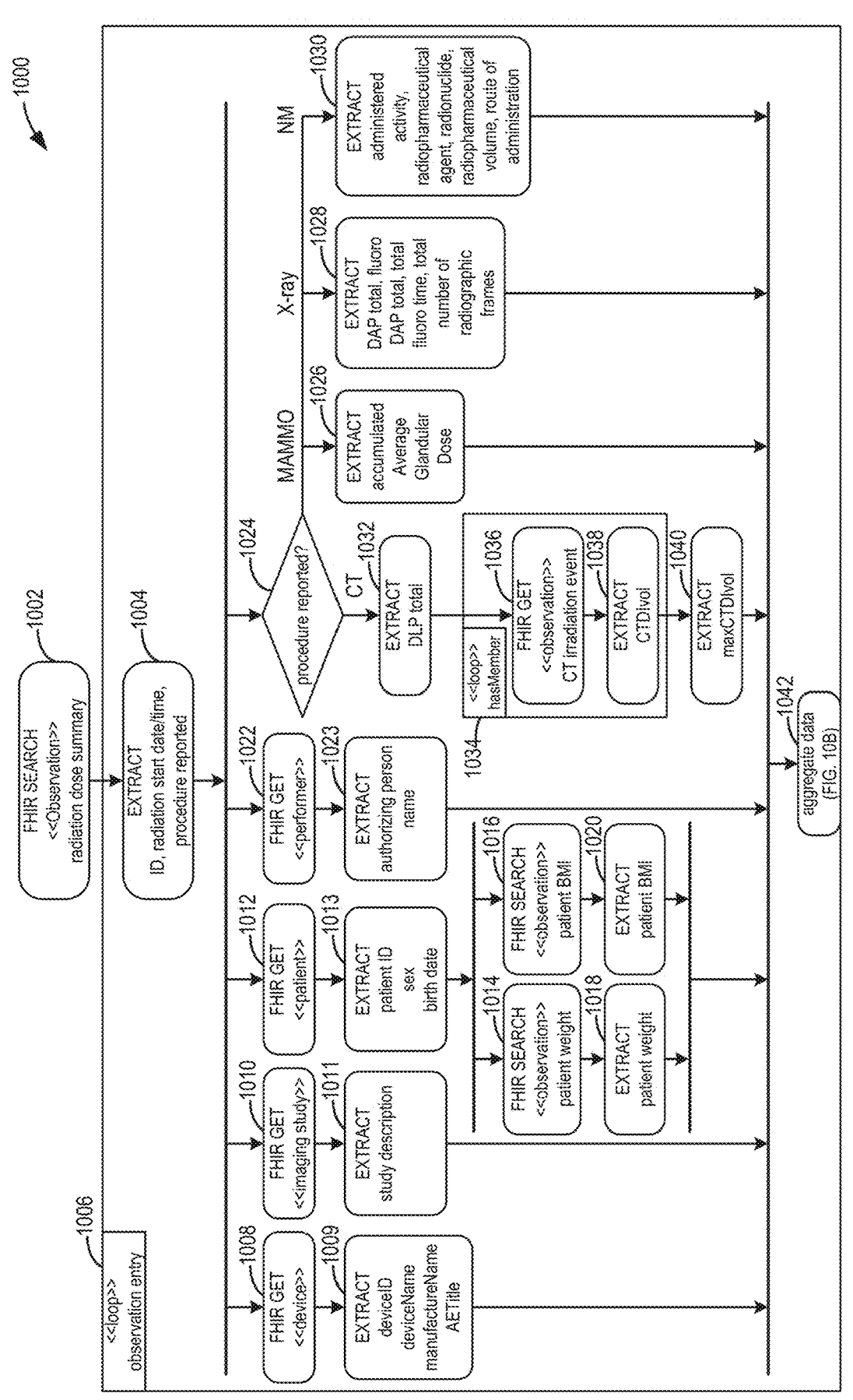
FIG. 10A is a flow chart illustrating an example method for a third example of radiation dose data extraction and aggregation, from the perspective of a web data connector.

As described herein, the interoperability system 118 may be configured as a FHIR® API, in some examples. FIG. 10A illustrates a flow chart for an example method for a third example of radiation dose data transmission, from the perspective of a web data connector (WDC). As described in FIG. 10A with respect to the FHIR® API, a specific defined subset of radiation dose data defined by the HL7® community is referred to as a "radiation dose summary". The FHIR® API is configured to search for observations requested by a request from a WDC (e.g., radiation dose data requested by a first request from the WDC 120) and extract information from retrieved resources. The WDC then aggregates extracted data. In the example described herein, the FHIR® API defines a plurality of resources, including a radiation observation resource, a patient resource, a performer (e.g., practitioner) resource, a device resource, an imaging study resource, and patient observations resources. The observation resource is used to describe the radiation dose summary and collected minimal dose information. The patient resource is used to reference an irradiated person. The practitioner resource is used to reference a related irradiation authorizing person. The device resource is used to describe an irradiating modality. The imaging study resource is used to reference a performed exam. An entry point for the radiation dose summary is the observation resource, which may follow the resources described in HL7® profiles to describe minimal radiation information. Further detail regarding radiation data collection through the FHIR® API and the interoperability system 118 are described herein.

At 1002, the WDC performs a search on the FHIR® API for the observation resource and obtains a radiation dose summary from a database, such as the RDD 116 of FIG. 1. The radiation dose summary may include a plurality of resources and other radiation dose data information, which is stored by the RDD 116, following the reception or radiation data from an imaging system (e.g., at least one of the imaging devices 102 of FIG. 1). The collected radiation dose data are formatted as radiation dose summary observation resources by the FHIR® API. At 1004, the WDC extracts from the FHIR® API a first set of information from the radiation dose summary. For example, the first set of information includes an identification (ID) of the radiation dose summary (e.g., a numerical identifier, a name, and so on), a date and a time at which the imaging procedure (e.g., radiation) to collect the radiation dose summary commenced, and a radiation procedure used to collect the radiation dose summary. The first set of information may further be comprised of one or more modality-specific (e.g., hospital modality-specific) radiation dose metrics. In some examples, extracting the first set of information may further comprise stripping data of the first set of information of the first format.

Operations of the WDC on the FHIR® API, including and following operation 1004, may be part of a loop 1006 performed by the WDC, which may allow information extracted from the radiation dose summary obtained at operation 1002 to be aggregated into a single file or other grouping. As further described herein, the FHIR® API may retrieve a plurality of radiation dose data from the RDD, such as a plurality of radiation dose data which have been acquired by the RDD (e.g., transmitted to the RRD from an imaging device, as described with respect to FIG. 5) within a time frame indicated by the request from the WDC. Operations of the WDC within the loop 1006 may be performed for each radiation dose summary retrieved by the WDC via the FHIR® API, such that resources of interest within each radiation dose summary may be stored as information accessible to a third-party tool (e.g., to the RDC 122), while still being connected to identifying information (e.g., the first set of information extracted at operation 1004).

Following extraction of the first set of information at operation 1004, the WDC identifies resources of the radiation dose summary and extracts a second set of information therefrom through the FHIR® API of the interoperability system 118. At 1008, the WDC identifies the device resource through the FHIR® API of the interoperability system and extracts information from the device resource including a device ID, a device name, a manufacture name, and an application entity (AE) title at 1009. At 1010, the WDC identifies the imaging study resource and extracts information therefrom, including a study description at 1011. At 1012, the WDC identifies the patient resource and extracts information therefrom, including patient ID, sex, and birth date at 1013. In some examples, further information may be desired from the patient resource. For example, as described with respect to the table 950 of FIG. 9B, some cohort levels (e.g., resources) may be desired for some radiation procedures and not for others. In the example shown in FIG. 10A, the radiation procedure may be computed tomography (CT) and the WDC may perform searches for observation resources related to the patient resource, such as a search for patient weight at 1014 and a search for patient BMI at 1016. The WDC may extract information regarding a patient weight at 1018 from the patient weight observation and may extract information regarding a patient BMI at 1020 from the patient BMI observation. At 1022, the WDC identifies the performer resource and extracts information therefrom, including an authorizing person name at 1023.

Briefly returning to operation 1004, extraction of the first set of information for the radiation dose summary may include identifying a procedure reported, e.g., the radiation procedure performed to collect information of the radiation dose summary. At 1024, the WDC may identify the reported procedure, which may be from mammography (MAMMO), X-ray, nuclear medicine (NM), or CT, for example. The WDC may extract metrics characteristic of each procedure, as described with respect to the table 900 of FIG. 9A. When MAMMO is the performed procedure, at 1026, the WDC may extract metrics including accumulated Average Glandular Dose (AGD). When X-ray is the performed procedure, at 1028, the WDC may extract metrics including DAP total, fluoro DAP total, total fluoro time, and total number of radiographic frames. When NM is the performed procedure, at 1030, the WDC may extract metrics including administered activity, radiopharmaceutical agent, radionuclide, radiopharmaceutical volume, and route of administration.

When CT is the performed procedure, as is the case in the example shown in FIG. 10A, at 1032, the WDC may extract metrics including DAP total. The WDC may further perform a second loop 1034 to identify an observation resource for CT irradiation events at 1036, which may include a plurality of events for a single radiation dose summary. For each CT irradiating event, the WDC may extract CTDIvol at 1038. Following extraction of at least one CTDIvol, at 1040, the WDC may calculate a maxCTDIvol of the plurality of CTDIvol extracted in the second loop 1034.

At 1042, the WDC may aggregate extracted information which forms the first set of information and the second set of information to generate a single file or grouping of information associated with the radiation dose summary, where the information is not formatted according to the first format in which the information is stored. In some examples, the information may be stored as raw data without formatting, and the information may be formatted by the RDC and/or by the WDC, as described above with respect to the first example and the second example for radiation dose data transmission. Further detail regarding aggregation of extracted information is described with respect to FIG. 10B. Information may be used by the RDC to generate dashboards for visualization, manipulation, and analysis of the data, as further described with respect to FIGS. 11 and 12.

Figure 10B:
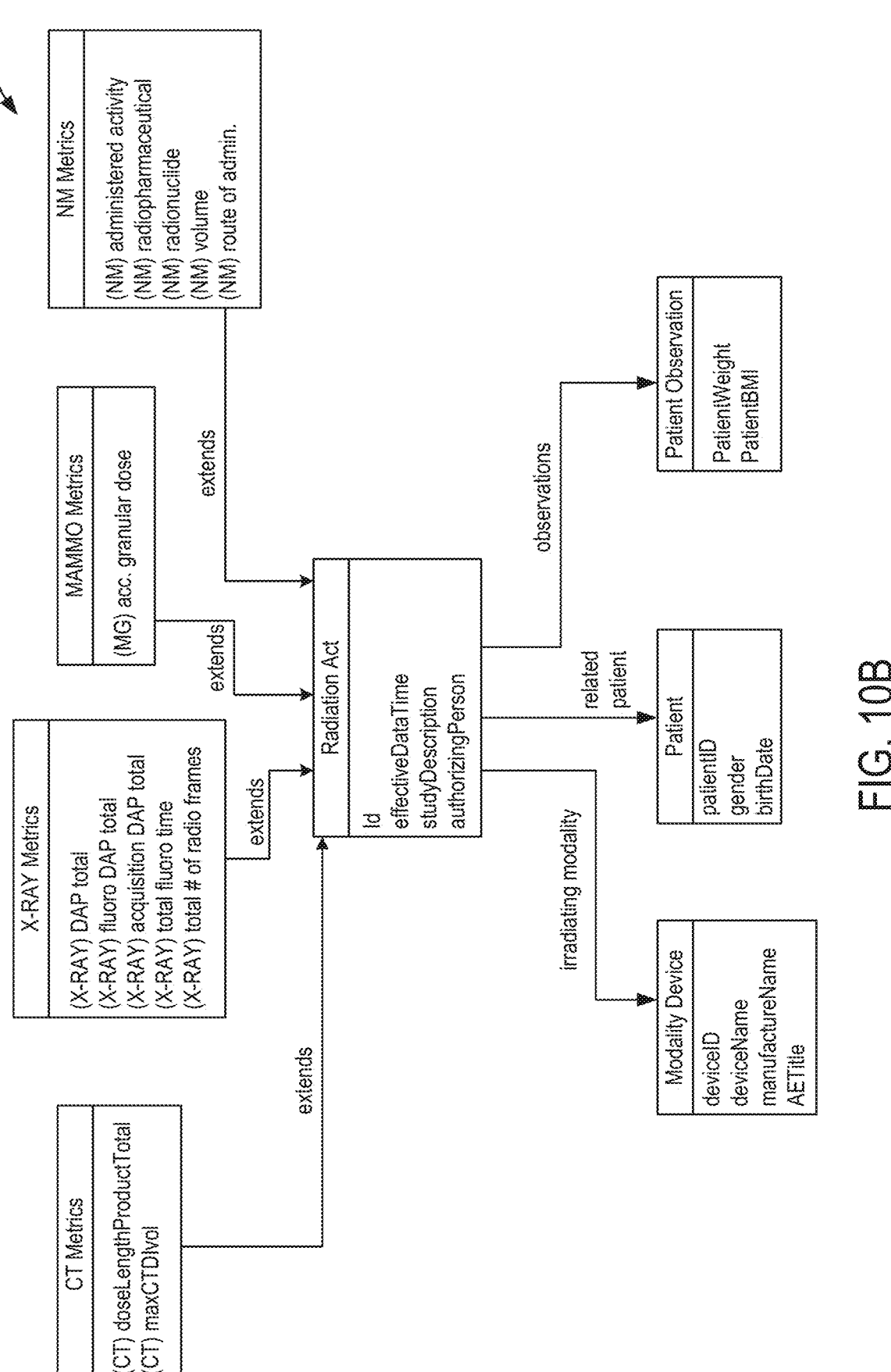
FIG. 10B shows an architecture used to aggregate extracted radiation dose data.

FIG. 10B shows an architecture 1050 used to aggregate extracted radiation dose data, as briefly described with respect to operation 1042 of FIG. 10A. In the example shown in FIG. 10B, extracted radiation dose data may be transformed into tables, which may be exploited by a third-party tool, as described with respect to FIGS. 11-12. The extracted radiation dose data may be stored in an aggregated format based on a hierarchy of data, for example.

An example use case for using the RDC 122 to generate a dashboard based on radiation dose data collected by a CT imaging system is as follows. The first set of information and the second set of information used to generate the dashboard may be extracted according to the first example, the second example, or the third example for transmission of radiation dose data. In some examples, the dashboard may obtain, detect, or otherwise receive user input representing a selection of a dose metric for analysis. For example, the user input may select total DLP, indicating a measure of CT tube radiation exposure, or maximum volume CT dose index (CTDIvol), representing radiation dose through a slice of an appropriate phantom (as described with respect to the first table 900). The user input may also include a selection of a plurality of cohort levels (e.g., up to three cohort levels) to be represented as levels of granularity. In some examples, the three cohort levels may together represent a hierarchy. Cohort levels may be selected from the cohort levels shown in the second table 950 which correspond to the CT system (e.g., device, manufacturer, model, study description, anatomical region, performing physician, and patient BMI, weight range, and/or sex). The dashboard generated by the RDC 122 may display statistics based on the metric selected and cohorts defined through different cohort levels. For example, statistics may include minimum, maximum, median, P10, P25, P50, and so on of the selected metrics. The statistics may be grouped based on the cohort of data for different defined cohort levels. The dashboard may further include distribution of the metric grouped based on cohorts selected, correlation analysis between the metric and the cohorts selected, and trend of the metric selected over time grouped through the cohorts selected.

Collected data may be used to provide metrics related to cumulative radiation doses administered to patients through a period of time for multiple procedures. For example, dose metrics calculated based on data collected by the interoperability system 118 may include CT cumulative DLP, X-ray cumulative DAP, and cumulative average glandular dose (AGD) for a specific performed exam. Cumulative radiation doses administered to patients is the sum of these metrics through a period of time and across multiple performed procedures. Cumulative radiation dose can be calculated over a period, such as the last month, the last three months, the last year, and so on. Also, cumulative radiation dose calculations can be calculated based on parameters other than period, such as the procedure type, the device type, and so on. Cumulative dose dashboards may allow identification of radiation behavior on patients and different aberrations.

Figure 11:
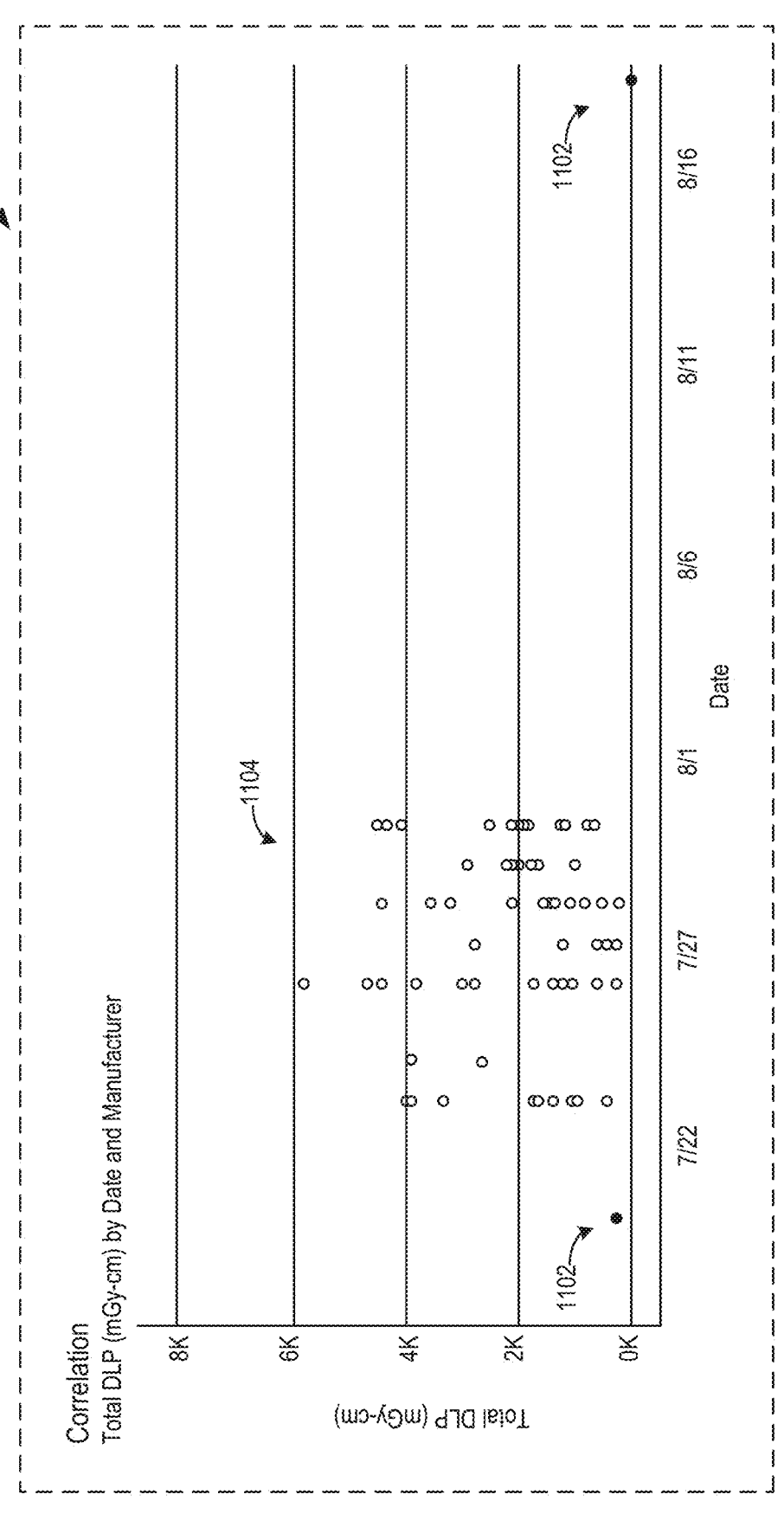
FIG. 11 shows a first example display of a dashboard generated based on radiation dose data.
Figure 12:
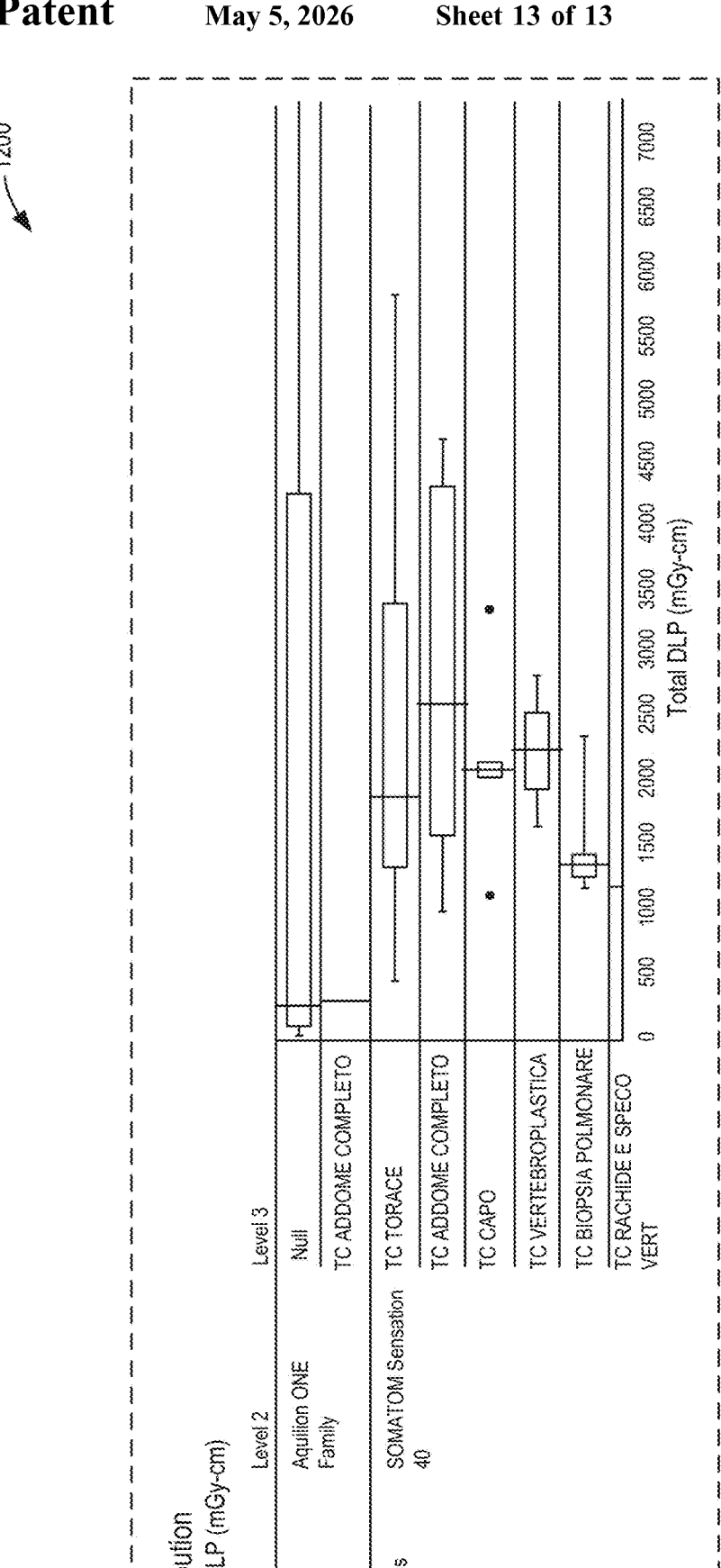
FIG. 12 shows a second example display of a dashboard generated based on radiation dose data.

Included herein are two example dashboards showing comparisons of DLP for different imaging procedures, manufactures, and imaging devices. However, other dashboards may be generated by the RDC 122 to be used for comparing these and other metrics and cohorts without departing from the scope of the present disclosure. FIG. 11 shows a first example dashboard 1100 and FIG. 12 shows a second example dashboard 1200, each of which may be generated by the RDC 122 based on radiation dose data. The RDC 122 may use radiation dose data which is stored in the second format (e.g., flat files), which may be different from the first format by which the radiation dose data is formatted when collected during an imaging procedure performed by an imaging device. The first example dashboard 1100 and/or the second example dashboard 1200 may be output for display on a display device, such as the display device 128 of the client device 124 of FIG. 1. A user may interact with the GUI 126 of the client device 124 to provide a user input, which represents selected metrics and cohorts' levels of the radiation dose data to be analyzed using a dashboard generated by the RDC 122.

The first example dashboard 1100 of FIG. 11 shows a correlation of total DLP by date and by manufacturer. Total DLP in mGy-cm is shown on the ordinate and date is shown on the abscissa. Characteristics of a plot point (e.g., color, shading, size, shape, etc.) indicate different manufactures. In the first example dashboard 1100 a first manufacture is indicated by black filled-in plot points 1102 and a second manufacturer is indicated by white filled-in plot points 1104. Each plot point may indicate a single radiation dose data (e.g., aggregation of the first set of information and the second set of information, as described with respect to operation 206 of the method 200). Each radiation dose data may be for a different patient, or some of the plot points may represent the same patient, for example, patients which have multiple imaging procedures performed during the time period shown in the first example dashboard 1100. In this way, the first example dashboard 1100 may show distribution of radiation dosage to which patients are exposed according to a manufacturer of the imaging device and over a selected time period.

The second example dashboard 1200 of FIG. 12 shows a correlation of total DLP by modality. A first column labeled "Level 1" indicates a manufacturer, herein a first manufacturer (e.g., Canon) and a second manufacturer (e.g., Siemens). A second column labeled "Level 2" indicates a device model name. A third column labeled "Level 3" indicates an imaging procedure performed. A fourth column (unlabeled) includes a box plot indicating a range of total DLP in mGy-cm for each imaging procedure of each imaging device. The box plot may indicate a maximum DLP, a minimum DLP, an average DLP, and an average DLP range. Box plots may be generated based on radiation dose data aggregated by the RDC 122 for a plurality of imaging procedures performed on a plurality of patients over time. Generation of the second example dashboard 1200 may enable comparison among different manufacturers and different imaging devices to determine potential radiation doses a patient may be exposed to when using an imaging device for a given imaging procedure. As explained above with respect to FIG. 2, at least one of the devices disclosed herein may be configured to output an alert based on the aggregated radiation dose data. For example, an alert may be generated when a total DLP, average DLP, average DLP range, etc., meets a condition relative to a threshold (e.g., the DLP is above a threshold) for a patient, a cohort of patients, a specific scanner/imaging system, a model type of scanners/imaging systems, a manufacturer of scanners/imaging systems, a medical/imaging facility, and so forth.

In this way, medical data—specifically radiation dose data—may be collected by a third-party tool from a database operably coupled to an imaging system without directly connecting the third-party tool to the database. By converting radiation dose data from a first format to a second format, wherein the second format is useable by the third-party tool, the methods described herein may allow processing of radiation dose data generated and/or stored according to a first format by third-parties which use a second format. Perpetual indexation (e.g., data collection) of radiation dose data by the radiation dose consumer (RDC) may allow the RDC to collect radiation dose data at a regular frequency (e.g., hourly, daily, weekly, etc.) from a radiation dose database (RDD) via an interoperability system and a web data connector (WDC). This may be beneficial when the database is a proprietary database, when the database stores additional information which is not of interest to the third-party tool, and/or when a data storage format of the database is different than a data use format of the third-party tool. The methods described herein allow agnostic connection of the RMS, including the RDD, to the RDC. Generation and display of dashboards by the RDC based on radiation dose data from the RDD may provide dynamic resources for accessing, analyzing, and comparing data among cohorts and metrics of the data. A dynamic nature of the generated dashboards may allow access to all collected metrics following different cohort levels of the radiation dose data. In this way, a vendor neutral, agnostic method and system are provided for transmission and analytics on radiation dose data.

The disclosure also provides support for a system, comprising: memory storing instructions executable by a processor to: retrieve radiation dose data in a first format from a radiation dose database via an interoperability system operably coupled to the radiation dose database, convert the radiation dose data to a second format usable by a radiation dose consumer, and generate visualizations of the radiation dose data in the second format for display on a display device. In a first example of the system, the first format comprises JSON and wherein the second format comprises flat files. In a second example of the system, optionally including the first example, the interoperability system comprises a Fast Health Interoperability Resources (FHIR®) application programming interface (API). In a third example of the system, optionally including one or both of the first and second examples to retrieve the radiation dose data in the first format, the instructions are executable to: send a request to the interoperability system to retrieve radiation dose data stored in the radiation dose database over a given time period, for radiation dose data received from the interoperability system: extract a first set of information from the radiation dose data, including a radiation procedure reported by the radiation dose data, send a plurality of additional requests to the interoperability system, each requesting a different aspect of the radiation procedure, receive a plurality of additional responses from the interoperability system, and extract a second set of information from the plurality of additional responses. In a fourth example of the system, optionally including one or more or each of the first through third examples to convert the radiation dose data to the second format, the instructions are executable to aggregate the extracted first set of information and the extracted second set of information in the second format. In a fifth example of the system, optionally including one or more or each of the first through fourth examples, the first set of information comprises an identification of the radiation dose data, a date and time at which the radiation procedure commenced, the radiation procedure information, and one or more modality-specific radiation dose metrics. In a sixth example of the system, optionally including one or more or each of the first through fifth examples, the second set of information comprises parameters of a device used to carry out the radiation procedure, an imaging study description of the radiation procedure, patient information of a patient imaged via the radiation procedure, patient observations, and performer information of a clinician who authorized and/or oversaw the radiation procedure. In a seventh example of the system, optionally including one or more or each of the first through sixth examples, visualizations of the radiation dose data in the second format include visualizations of cumulative radiation dose data through a period of time and/or over multiple performed procedures. In an eighth example of the system, optionally including one or more or each of the first through seventh examples, the memory stores instructions further executable by the processor to generate an alert in response to converted radiation dose data exceeding a threshold.

The disclosure also provides support for a system, comprising: a radiation dose database communicatively coupled to a plurality of imaging devices, a processor, and memory storing instructions executable by the processor to: receive a first request to send radiation dose data to a radiation dose consumer, in response to the first request, retrieve the radiation dose data from the radiation dose database and send the radiation dose data to the radiation dose consumer, wherein the radiation dose data is formatted according to a Fast Healthcare Interoperability Resources (FHIR®) standard, receive a second request to send additional parameters related to the radiation dose data to the radiation dose consumer, the additional parameters including information identifying an imaged patient associated with the radiation dose data, a study description of an imaging study carried out to image the imaged patient, information identifying an imaging device used to image the imaged patient, and/or information identifying a clinician that authorized the imaging study, and in response to the second request, retrieve the additional parameters from the radiation dose database and send the additional parameters to the radiation dose consumer, wherein the additional parameters are formatted according to the FHIR® standard. In a first example of the system, different additional parameters are retrieved for different imaging procedures performed by different imaging devices, wherein: additional parameters for mammography includes accumulated average glandular dose (AGD), additional parameters for X-ray include dose area product (DAP) total, fluoro DAP total, total fluoro time, and number of radiographic frames, additional parameters for nuclear medicine include administered activity, radiopharmaceutical agent, radionuclide, route of administration, and radiopharmaceutical volume, and additional parameters for computed tomography include total dose length product (DLP) and max CT dose index volume (CTDIvol). In a second example of the system, optionally including the first example, the information identifying the imaged patient includes a patient ID, a patient sex, a patient birth date, a patient body mass index (BMI), and a patient weight. In a third example of the system, optionally including one or both of the first and second examples, the study description is included in an imaging study resource. In a fourth example of the system, optionally including one or more or each of the first through third examples, information identifying the imaging device includes a device ID, a device name, a manufacture name, and an application entity (AE) title. In a fifth example of the system, optionally including one or more or each of the first through fourth examples, information identifying the clinician that authorized the imaging study includes an authorizing person name.

The disclosure also provides support for a system, comprising: a radiation dose database communicatively coupled to a plurality of imaging devices, an interoperability system operatively coupled to the radiation dose database, and a radiation dose consumer communicatively coupled to the interoperability system, wherein: the interoperability system is configured to retrieve radiation dose data from the radiation dose database and send the radiation dose data to the radiation dose consumer, the radiation dose data formatted according to a Fast Healthcare Interoperability Resources (FHIR®) standard, the radiation dose consumer is configured to extract selected information from the radiation dose data, store the extracted selected information in a flat file, and generate one or more dashboards from the extracted selected information for display on a display device. In a first example of the system, the interoperability system is configured to retrieve and send the radiation dose data in response to a first request from the radiation dose consumer, and wherein the interoperability system is further configured to, in response to receiving a second request from the radiation dose consumer to send additional parameters related to the radiation dose data, retrieve the additional parameters from the radiation dose database and send the additional parameters to the radiation dose consumer, the additional parameters including information identifying an imaged patient associated with the radiation dose data, a study description of an imaging study carried out to image the imaged patient, information identifying an imaging device used to image the imaged patient, and information identifying a clinician that authorized the imaging study, wherein the additional parameters are formatted according to the FHIR® standard. In a second example of the system, optionally including the first example, information collected in response to receiving the second request is sorted into metrics including: total dose length product (DLP), maximum computed tomography dose index volume (CTDIvol), accumulated average glandular dose (AGD), dose area product (DAP) total, fluoro DAP total, acquisition total DAP, total fluoro time, administered activity, and radiopharmaceutical volume, and cohorts including: radiopharmaceutical agent, radionuclide, route of administration, patient sex, patient body mass index (BMI), patient weight, device ID and/or device name, a manufacture name, performing physician, anatomical region, and study description. In a third example of the system, optionally including one or both of the first and second examples, the one or more dashboards include a comparison of metrics and cohorts of the radiation dose data. In a fourth example of the system, optionally including one or more or each of the first through third examples, the interoperability system is configured to retrieve a plurality of radiation dose data which have been added to the radiation dose database for storage in a given time period.

FIG. 1 shows example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, an element or step recited in the singular and preceded with the word "a" or "an" should be understood as not excluding plural of said elements or steps, unless such exclusion is explicitly stated. Furthermore, references to "one example" of the present invention are not intended to be interpreted as excluding the existence of additional examples that also incorporate the recited features. Moreover, unless explicitly stated to the contrary, examples "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
an interoperability system comprising memory storing instructions executable by one or more processors and communicatively coupled to a radiation dose database;
a radiation dose consumer comprising memory storing instructions executable by one or more processors, the radiation dose consumer communicatively coupled to the interoperability system via a web data connector, the interoperability system communicatively coupled between the radiation dose database and the radiation dose consumer, the system configured to:
retrieve, via the interoperability system, radiation dose data in a first format from the radiation dose database, the retrieving including the interoperability system retrieving the radiation dose data from the radiation dose database and transmitting the retrieved radiation dose data in the first format to the web data connector;
convert, via the web data connector, the radiation dose data to a second format usable by the radiation dose consumer; and
process, via the radiation dose consumer, the radiation dose data in the second format to generate visualizations of the radiation dose data and send the visualizations to a client device for display on a display device of the client device, wherein the web data connector is executed on the radiation dose consumer or a server.

2. The system of claim 1, wherein the first format comprises JSON and wherein the second format comprises flat files.

3. The system of claim 1, wherein the interoperability system comprises a Fast Health Interoperability Resources (FHIR®) application programming interface (API).

4. The system of claim 1, wherein, to retrieve the radiation dose data in the first format, the system is configured to:

send, via the web data connector, a request to the interoperability system to retrieve all radiation dose summaries stored in the radiation dose database over a given time period;

for a selected radiation dose summary:

extract a first set of information from the selected radiation dose summary, including a radiation procedure reported by the radiation dose summary;

based on the first set of information, send a plurality of additional requests to the interoperability system, each requesting a different aspect of the radiation procedure;

receive a plurality of additional responses from the interoperability system; and extract a second set of information from the plurality of additional responses.

5. The system of claim 4, wherein, to convert the radiation dose data to the second format, the web data connector is configured to aggregate the extracted first set of information and the extracted second set of information in the second format.

6. The system of claim 4, wherein the first set of information comprises an identification of the selected radiation dose summary, a date and time at which the radiation procedure commenced, the radiation procedure information, and one or more modality-specific radiation dose metrics, and wherein each radiation dose summary is a subset of radiation dose data defined by the HL7® format.

7. The system of claim 6, wherein the second set of information comprises parameters of a device used to carry out the radiation procedure, an imaging study description of the radiation procedure, patient information of a patient imaged via the radiation procedure, patient observations, and performer information of a clinician who authorized and/or oversaw the radiation procedure.

8. The system of claim 1, wherein visualizations of the radiation dose data in the second format include visualizations of cumulative radiation dose data through a period of time and/or over multiple performed procedures.

9. The system of claim 1, wherein the system is configured to generate an alert in response to converted radiation dose data exceeding a threshold.

10. A system, comprising:

an interoperability system communicatively coupled between a radiation dose consumer and a radiation dose database communicatively coupled to a plurality of imaging devices, the interoperability system comprising:

a processor; and memory storing instructions executable by the processor to:

receive, from a web data connector communicatively coupled to the interoperability system, a first request to send radiation dose data to a radiation dose consumer, the radiation dose consumer comprising memory storing instructions and one or more processors;

in response to the first request, retrieve the radiation dose data from the radiation dose database and send the radiation dose data to the radiation dose consumer via the web data connector, wherein the radiation dose data is a radiation dose summary of a radiation procedure formatted according to a Fast Healthcare Interoperability Resources (FHIR®) standard;

receive, from the web data connector, a second request to send additional parameters related to the radiation dose data to the radiation dose consumer, the additional parameters including information identifying an imaged patient associated with the radiation dose data, a study description of an imaging study carried out to image the imaged patient, information identifying an imaging device used to image the imaged patient, and/or information identifying a clinician that authorized the imaging study; and in response to the second request, retrieve the additional parameters from the radiation dose database and send the additional parameters to the radiation dose consumer via the web data connector, wherein the additional parameters are formatted according to the FHIR® standard, and wherein the web data connector is executed on the radiation dose consumer or a server.

11. The system of claim 10, wherein:

if the radiation procedure is mammography, the radiation dose data include accumulated average glandular dose (AGD);

if the radiation procedure is X-ray, the radiation dose data include dose area product (DAP) total, fluoro DAP total, total fluoro time, and number of radiographic frames;

if the radiation procedure is nuclear medicine, the radiation dose data include administered activity, radiopharmaceutical agent, radionuclide, route of administration, and radiopharmaceutical volume; and if the radiation procedure is computed tomography, the radiation dose data include total dose length product (DLP) and the additional parameters include max CT dose index volume (CTDIvol).

12. The system of claim 10, wherein the information identifying the imaged patient includes a patient ID, a patient sex, a patient birth date, a patient body mass index (BMI), and a patient weight.

13. The system of claim 10, wherein the study description is included in an imaging study resource.

14. The system of claim 10, wherein information identifying the imaging device includes a device ID, a device name, a manufacture name, and an application entity (AE) title.

15. The system of claim 10, wherein information identifying the clinician that authorized the imaging study includes an authorizing person name.

16. A system, comprising:

a radiation dose database communicatively coupled to a plurality of imaging devices;

an interoperability system operatively coupled to the radiation dose database and comprising memory storing instructions executable by one or more processors; and a radiation dose consumer communicatively coupled to the interoperability system and comprising memory storing instructions executable by one or more processors, the radiation dose consumer communicatively coupled to the interoperability system via a web data connector, wherein:

the interoperability system is configured to retrieve radiation dose data from the radiation dose database, the radiation dose data formatted according to a Fast Healthcare Interoperability Resources (FHIR®) standard, wherein the data in the FHIR format includes data in JSON format, and wherein the retrieving includes the interoperability system retrieving the radiation dose data from the radiation dose database and transmitting the retrieved radiation dose data in the JSON format to the web data connector;

the web data connector is configured to extract selected information from the radiation dose data in the JSON format and convert the selected information in the JSON format to a flat file; and the radiation dose consumer is configured to process the extracted selected information in the flat file to generate one or more dashboards and send the one or more dashboards to a client device for display on a display device of the client device, wherein the web data connector is executed on the radiation dose consumer or a server.

17. The system of claim 16, wherein the interoperability system is configured to retrieve and send the radiation dose data in response to a first request from the web data connector, wherein the interoperability system is further configured to, in response to receiving a second request from the web data connector to send additional parameters related to the radiation dose data, retrieve the additional parameters from the radiation dose database and send the additional parameters to the web data connector, the additional parameters including information identifying an imaged patient associated with the radiation dose data, a study description of an imaging study carried out to image the imaged patient, information identifying an imaging device used to image the imaged patient, and information identifying a clinician that authorized the imaging study, and wherein the additional parameters are formatted according to the FHIR® standard.

18. The system of claim 17, wherein the radiation dose data and the information collected in response to receiving the second request is sorted into metrics, including: total dose length product (DLP), maximum computed tomography dose index volume (CTDIvol), accumulated average glandular dose (AGD), dose area product (DAP) total, fluoro DAP total, acquisition total DAP, total fluoro time, administered activity, and radiopharmaceutical volume; and cohorts, including: radiopharmaceutical agent, radionuclide, route of administration, patient sex, patient body mass index (BMI), patient weight, device ID and/or device name, a manufacture name, performing physician, anatomical region, and study description.

19. The system of claim 18, wherein the one or more dashboards include a comparison of metrics and cohorts of the radiation dose data.

20. The system of claim 16, wherein the radiation dose data is formatted as a radiation dose summary for a selected radiation procedure, and wherein the interoperability system is configured to retrieve a plurality of radiation dose summaries which have been added to the radiation dose database for storage in a given time period.

* * * * *